(12) United States Patent
Tabic et al.

(10) Patent No.: US 12,310,370 B2
(45) Date of Patent: May 27, 2025

(54) METHODS FOR REARING AND CONTROLLED RELEASE OF BIOLOGICAL CONTROL AGENTS

(71) Applicant: Bio-Bee SDE Eliyahu Ltd., Emmek H'maayanot (IL)

(72) Inventors: Arnon Tabic, Emmek H'maayanot (IL); Tom Katz, Emmek H'maayanot (IL); Amir Grosman, Emmek H'maayanot (IL); Shimon Steinberg, Emmek H'maayanot (IL)

(73) Assignee: BIO-BEE SDE ELIYAHU LTD., Emmek H'maayanot (IL)

( * ) Notice: Subject to any disclaimer, the term of this patent is extended or adjusted under 35 U.S.C. 154(b) by 715 days.

(21) Appl. No.: 16/976,009

(22) PCT Filed: Mar. 5, 2019

(86) PCT No.: PCT/IL2019/050242
§ 371 (c)(1),
(2) Date: Aug. 26, 2020

(87) PCT Pub. No.: WO2019/171374
PCT Pub. Date: Sep. 12, 2019

(65) Prior Publication Data
US 2021/0100250 A1  Apr. 8, 2021

(30) Foreign Application Priority Data
Mar. 5, 2018 (IL) .......................................... 257892

(51) Int. Cl.
*A01K 67/033* (2006.01)
*A01N 63/16* (2020.01)

(52) U.S. Cl.
CPC ............ *A01N 63/16* (2020.01); *A01K 67/033* (2013.01)

(58) Field of Classification Search
CPC ....... A01K 67/033; A01N 63/16; A01N 63/00
(Continued)

(56) References Cited

U.S. PATENT DOCUMENTS 4,646,683 A * 3/1987 Maedgen, Jr. ....... A01K 67/033
119/6.5
6,129,935 A * 10/2000 White .................... A23K 50/90
119/6.5
(Continued)

FOREIGN PATENT DOCUMENTS

EP   1 830 631 B1   5/2010
EP   2 380 436 B1   10/2012
(Continued)

OTHER PUBLICATIONS

Beaulieu, F. and Knee, W., "Plant-feeding mites of the Canadian Prairies", Arthropods of Canadian Grasslands, 2014, vol. 3, pp. 29-72.
(Continued)

*Primary Examiner* — Monica L Perry
*Assistant Examiner* — Aaron M Rodziwicz
(74) *Attorney, Agent, or Firm* — Gary J. Gershik

(57) ABSTRACT

A rearing composition comprising: predatory mite population comprising at least one mite species of the genus *Phytoseiulus*, and a prey mite population comprising at least one species from the order Astigmata or from the family Phytoseiidae.

19 Claims, 8 Drawing Sheets

(58) Field of Classification Search
USPC .................................................. 119/6.5, 6.6
See application file for complete search history.

(56) References Cited

U.S. PATENT DOCUMENTS

| | | | |
|---|---|---|---|
| 7,947,269 | B2 | 5/2011 | Bolckmans et al. |
| 8,097,248 | B2 | 1/2012 | Bolckmans et al. |
| 8,957,279 | B2 | 2/2015 | Bolckmans et al. |
| 9,693,540 | B2 * | 7/2017 | Bolckmans ............ A01N 63/14 |
| 9,781,937 | B2 * | 10/2017 | Bolckmans .......... A01K 67/033 |
| 2005/0178337 | A1 * | 8/2005 | Wright ................. A01K 67/033 |
| | | | 119/6.5 |
| 2013/0202714 | A1 | 8/2013 | Vila Rifa et al. |
| 2014/0178490 | A1 * | 6/2014 | Steinberg ............... A01N 63/00 |
| | | | 424/538 |
| 2015/0128864 | A1 | 5/2015 | Bolckmans et al. |
| 2015/0128884 | A1 | 5/2015 | Pursifull et al. |
| 2015/0296759 | A1 | 10/2015 | Guichou et al. |
| 2018/0160688 | A1 | 6/2018 | Vila Rifa et al. |
| 2020/0113187 | A1 | 4/2020 | Steinberg et al. |

FOREIGN PATENT DOCUMENTS

| | | |
|---|---|---|
| EP | 2 866 567 B1 | 7/2016 |
| EP | 3 527 072 A1 | 8/2019 |
| ES | 2 533 918 | 4/2015 |
| WO | WO 2013/103295 A1 | 7/2013 |
| WO | 13/190412 A1 | 12/2013 |
| WO | 19/017776 A1 | 1/2019 |

OTHER PUBLICATIONS

Kanouh, M., et al., "Phylogenetic and biogeographic analysis of the genus *Phytoseiulus* (Acari: Phytoseiidae)", Zoologica Scripta, 2010, vol. 39, No. 5, pp. 450-461.

Moraes, G.J. et al., "A revised catalog of the mite family Phytoseiidae", ZooTaxa, 2004, vol. 434, No. 1, abstract, doi: http://dx.doi.org/10.11646/zootaxa.434.1.1.

Elhalawany, A.S. et al., "Influence of Prey Type on the Biology and Life-Table Parameters of *Neoseiulus californicus* (McGregor) (Acari: Phytoseiidae)", Acarines, 2017, vol. 11, pp. 15-20.

Knapp. M. et al., "Use of predatory mites in commercial biocontrol: current status and future prospects", Acarologia, 2018, vol. 58, pp. 73-82.

McMurtry, J.A. et al., "Revision of the lifestyles of phytoseiid mites (Acari: Phytoseiidae) and implications for biological control strategies", Molecules, 2013, vol. 18, No. 4 pp. 297-320.

Messelink, G.J. et al., "Pest species diversity enhances control of spider mites and whiteflies by a generalist phytoseiid predator", BioControl, 2010, vol. 55, pp. 387-398.

Moghadasi, M. et al., "Life Table and Predation Capacity of *Phytoseiulus persimilis* Athias-Henriot (Acari: Phytoseiidae) Feeding on *Tetranychus urticae* Koch (Acari: Tetranychidae) on Rose", J. Agr. Sci. Tech., 2016, vol. 18, pp. 1279-1288.

International Search Report issued by the International Searching Authority (ISA/O.E.P.M.) on Jun. 13, 2019 in connection with International Application No. PCT/IL2019/050242.

Jun. 13, 2019 Written Opinion issued in connection with PCT International Application No. PCT/IL2019/050242.

McMurtry, J. A., & Croft. B. A. (1997). Life-styles of phytoselid mites and their roles in biological control. *Annual review of entomology*, 42(1), 291-321.

McMurtry, J. A., De Moraes, G. J., & Sourassou, N. F. (2013). Revision of the lifestyles of phytoseiid mites (Acari: Phytoseiidae) and implications for biological control strategies. *Systematic and Applied Acarology*, 18(4), 297-320.

Aug. 2, 2024 Office Action issued in connection with Chilean Patent Application 202002142 and English machine translation thereof.

Jun. 7, 2024 First Examination Report issued in connection with Australian Patent Application No. 2019232660.

Aug. 21, 2024 First Examination Report issued in connection with Australian Patent Application No. 2019232660.

English translation of Mar. 24, 2022 Office Action issued in connection with Chilean Patent Application 202002142.

English translation of Apr. 29, 2022 Office Action issued in connection with Eurasian Patent Application 202091937/28 including English translation thereof.

English translation of Jun. 8, 2022 Office Action issued in connection with Chinese Patent Application 201980016699.1 including English translation thereof.

English translation of Oct. 20, 2022 Office Action issued in connection with Moroccan Patent Application 51117 including English translation thereof.

Nov. 8, 2022 Office Action issued in connection with Japanese Patent Application 2020-570662 including English translation thereof.

Jan. 16, 2023 English translation of the Office Action issued in connection with Eurasian Patent Application 202091937/28 including English translation thereof.

May 15, 2023 Office Action issued in connection with Israeli Patent Application No. 277031 including English Machine Translation thereof.

May 16, 2023 Office Action issued in connection with Japanese Patent Application 2020-570662 including English translation thereof.

Sep. 12, 2023 Office Action issued in connection with Canadian Patent Application 3,092,594 including English translation thereof.

Sep. 12, 2023 Office Action issued in connection with Chilean Patent Application 202002142 including English translation thereof.

English translation of Nov. 22, 2023 Office Action issued in connection with Brazilian Patent Application BR112020016640-5 including English translation thereof.

Nov. 28, 2023 Communication pursuant to Article 94(3) EPC issued in connection with European Patent Application 19 763 587.3.

English translation of Feb. 6, 2024 Office Action issued in connection with South Korean Patent Application 10-2020-7025096 including English translation thereof.

Aug. 8, 2024 Office Action in connection with Brazilian Patent Application BR112020016640-5 including English translation thereof.

Oct. 30, 2024 Office Action issued in connection with corresponding Korean Patent Application No. 10-2020-7025096, including English machine tranlation thereof.

Nov. 6, 2024 Office Action issued in connection with corresponding Ukrainian Patent Application No. 2020 05859, including English machine tranlation thereof.

Nov. 13, 2024 Office Action issued in connection with corresponding Mexican Patent Application No. Mx/a/2020/009205, including English machine tranlation thereof.

Nov. 18, 2024 Office Action issued in connection with corresponding Brazillian Patent Application No. BR112020016640-5, including English machine tranlation thereof.

\* cited by examiner

METHODS FOR REARING AND CONTROLLED RELEASE OF BIOLOGICAL CONTROL AGENTS

BACKGROUND OF THE INVENTION

Field of the Invention

The present invention relates to the field of biological control agents for crop protection, and more particularly to novel means and methods for rearing biological control agents against plant pests.

Background Art

The use of arthropods (insects and mites) as Biological Control Agents (BCA) is an expanding field with many advantages over chemical pest control. Arthropod BCA's are able to naturally control other arthropod species that act as pests on the crop.

*Phytoseiulus* is a genus of mites in the Phytoseiidae family. This predatory mite is the most frequently used to control two-spotted spider mites in greenhouses and outdoor crops grown in mild environments. A *Phytoseiulus* mite can consume up to seven adult spider mites or several dozens of their eggs in a day. A well-fed female lays about 50 eggs in her lifetime. The genus *Phytoseiulus* contains four known species, namely: *P. persimilis, P. longipes, P. macropilis* and *P. fragariae* (Chant and McMurtry 2006). All species of the genus *Phytoseiulus* are considered type 1 predators, i.e. highly specific to a diet consisting of spider mites, preferably of the genus *Tetranychus* (McMurtry and Croft 1997). The most frequently used species of this genus for biological control of spider mites is *Phytoseiulus persimilis*.

*Phytoseiulus persimilis* (*P. persimilis*) adults are bright reddish-orange in color, with long legs and pear-shaped bodies (about 0.5 mm long).

*P. persimilis* is considered as a specialist for spider mites (mites of the family Tetranychidae) which are phytophagous mites (Helle and Sabelis 1985, Gerson et al. 2003). Gerson et al. 2003 specifically indicate that "members of the genus *Phytoseiulus* live and place their eggs almost exclusively within the webbed colonies of *Tetranychus* spp". It is further noted in Gerson et al. 2003 that "the specificity of *P. persimilis* for spider mite prey can be a disadvantage if other predators are present on the same plants".

It was found that *P. persimilis* might develop and possibly reproduce on another phytophagous (plant feeding) mite, *Steneotarsonemus pallidus* of the family Tarsonemidae (Simmonds, S. P., 1970)

From a commercial point of view, a significant disadvantage of producing a predatory mite that exclusively feeds on phytophagous mites, such as spider mites, is that it requires rearing prey mites on plants, which has a high cost.

Walzer and Schausberger, 1999, examined intra- and interspecific predation of adult females and immature stages of the more generalist *Neoseiulus californicus* and the specialist *Phytoseiulus persimilis*. It was reported that adult females and immatures of both predators exhibited higher predation rates on larvae than on eggs and protonymphs. It was found that predation on *P. persimilis* by *N. californicus* was more severe than vice versa. *P. persimilis* was reported to have higher predation rates on conspecifics than heterospecifics and was more prone to cannibalism than *N. californicus*. In addition, it was reported that when provided with phytoseiid prey, *P. persimilis* suffered higher mortality than *N. californicus*.

Walzer and Schausberger, 1999 further teach that females of *P. persimilis* were not able to sustain oviposition, irrespective of con- or heterospecific prey. Furthermore, mortality of *P. persimilis* immatures was less when feeding on conspecific vs. heterospecific larvae. These authors concluded that for *P. persimilis*, neither hetero-nor conspecific prey provides sufficient nourishment for sustained reproduction. This is supported by Yao and Chant (1989), reporting that *P. persimilis* did not produce eggs when either cannibalizing or preying upon immatures of *Iphyseius degenerans*. There were only two females in this study that laid a single egg when cannibalizing conspecific.

In summary, it was found that *P. persimilis* was able to develop on juvenile predatory mites *Neoseiulus californicus* and *Iphyseius degenerans* of the family Phytoseiidae. However, it did not lay eggs when feeding on these prey mites. On the other hand, when the predatory mite *N. californicus* and *I. degenerans* fed on *P. persimilis*, they did lay eggs (Yao and Chant, 1989). This demonstrates the narrow dietary range of *P. persimilis* in contrast to other mites of the same family.

*P. persimilis* might also develop in a cannibalistic manner, feeding on younger stages of its own. When feeding this way, there were rare cases of oviposition (Walzer and Schausberger, 1999; Yao and Chant, 1989). In all cases where the Phytoseiidae mites were used as prey, the latter was fed with spider mites, which are grown on plants and therefore involves high costs.

*P. persimilis* was further found to develop on thrips (a phytophagous insect) larvae, but it did not lay eggs on this diet (Walzer 2004). This is in contrast to the predatory mite *N. californicus* that was able to reproduce on this prey (Walzer 2004). It should be emphasized that in this study, a high rate of mortality was reported during juvenile development.

U.S. Pat. No. 9,781,937 and EP patent 2612551 disclose a mite composition comprising predatory mite species selected from Mesostigmatid mite species or Prostigmatid mite species and a food source for the predatory mite species comprising Astigmatid mite species. It is further disclosed in these publications that at least a fraction of the Astigmatid individuals is immobilized and that the immobilized Astigmatid individuals are contacted with a fungus reducing agent comprising a fungus reducing mite population selected from a mycophagous mite species or an antifungal exudates producing mite species.

U.S. Pat. No. 7,947,269 teaches a mite composition comprising a rearing population of a phytoseiid predatory mite species and a factitious host population comprising at least one species selected from the family of the Carpoglyphidae.

U.S. Pat. No. 8,097,248 discloses a mite composition comprising a rearing population of the phytoseiid predatory mite species *Amblyseius swirskii*, a factitious host population comprising at least one Astigmatid mite species selected from the group consisting of: i) Carpoglyphidae, ii) Pyroglyphidae, and iii) Glyciophagidae.

U.S. Pat. No. 8,733,283 discloses a method for rearing predatory mites by providing a food source for prey mites that comprises dextrose; rearing *Thyreophagus entomophagus* prey mites on said food source; providing predatory mites that feed on *Thyreophagus entomophagus* in a starting ratio of predatory mites to prey mites from 1:10 to 1:100, and rearing the predatory mites on said prey mites, to create a breeding population.

U.S. Pat. No. 8,733,283 and EP2048941 patents teach that *Phytoseiulus persimilis* can be only raised on spider mite diet. They report that *P. persimilis* is an obligate spider mite predator and cannot survive on alternate food sources such as pollen. It is emphasized in these publications that survival tends to be poor if prey is in short supply.

EP2380436 discloses a mite composition comprising a rearing population of a phytoseiid predatory mite species and a population of at least one species from the order Astigmata characterized in that the population of the species from the order Astigmata is not alive.

WO2007075081 discloses mite composition comprising a rearing population of a phytoseiid predatory mite species and a factitious host population characterised in that the factitious host population comprises at least one species selected from the family of the Glyciphagidae. When referring to the phytoseiid mite *Phytoseiulus persimilis*, it is indicated that spider mites (*Tetranychus urticae*) is the best prey.

None of the above patent documents discloses or teaches successfully rearing the important predatory mite *Phytoseiulus persimilis* on mites of the order Astigmata, in any form or developmental stage. On the contrary, all the above patent documents and scientific publications report that *P. persimilis* is an obligate spider mite predator and it cannot survive on alternate food sources. Therefore, an entomologist/acarologist would not consider *P. persimilis* as a typical generalist species of the Phytoseiidae family or the Amblyseiinae subfamily but rather a highly specific species.

In view of the above, there is a long felt need for effective and efficient mass rearing of *Phytoseiulus persimilis* for biological control of crop pests.

SUMMARY OF THE INVENTION

The present invention relates to the field of insect control and more specifically to a system and method for rearing biological control agents against plant pests.

It is one object of the present invention to disclose a rearing composition comprising: predatory mite population comprising at least one mite species of the genus *Phytoseiulus*, and a prey mite population comprising at least one species from the order Astigmata.

It is a further object of the present invention to provide a rearing composition comprising: a predatory mite population comprising at least one mite species of the genus *Phytoseiulus*, and a prey mite population comprising individuals of at least one mite species from the order Astigmata, wherein said predatory mite population is capable of oviposition for at least 2 generations, further wherein said Astigmata prey is selected from the group consisting of non-viable mites, non-viable eggs and a combination thereof.

It is a further object of the present invention to disclose the rearing composition as defined in any of the above, wherein said predatory mite is capable of oviposition for at least 10 generations reared on said Astigmata prey individuals.

It is a further object of the present invention to disclose the rearing composition as defined in any of the above, wherein said predatory mite population exhibits an increased reproduction rate trait as compared to a control predatory mite population lacking said trait.

It is a further object of the present invention to disclose the rearing composition as defined in any of the above, wherein said predatory mite population exhibits a daily reproduction rate in the range of about 1.15-1.2.

It is a further object of the present invention to disclose the rearing composition as defined in any of the above, wherein said predatory mite population is characterized by a beige-white color.

It is a further object of the present invention to disclose the rearing composition as defined in any of the above, wherein said composition is absent of a fungus reducing agent.

It is a further object of the present invention to disclose the rearing composition as defined in any of the above, wherein said predatory mite species is selected from the group consisting of *Phytoseiulus fragariae*, *Phytoseiulus longipes*, *Phytoseiulus macropilis*, *Phytoseiulus persimilis* and *Phytoseiulus robertsi*.

It is a further object of the present invention to disclose the rearing composition as defined in any of the above, wherein said predatory mite species is *Phytoseiulus persimilis*.

It is a further object of the present invention to disclose the rearing composition as defined in any of the above, wherein the species from the order Astigmata is belonging to a family selected from the group consisting of Carpoglyphidae, Pyroglyphidae, Acaridae and Glycyphagidae.

It is a further object of the present invention to disclose the rearing composition as defined in any of the above, wherein the species from the order Astigmata comprises members from the family Carpoglyphidae, such as the genus *Carpoglyphus*, e.g. *Carpoglyphus lactis*, *Carpoglyphus munroi*; from the family Glycyphagidae such as the genus *Glycyphagus*, e.g. *Glycyphagus domesticus*, from the genus *Lepidoglyphus*, e.g. *Lepidoglyphus destructor*; from the family Pyroglyphidae such as the genus *Dermatophagoides*, e.g. *Dermatophagoides farinae*, *Dermatophagoides pteronisinus*, form the family Acaridae, such as the genus *Tyrophagus*, e.g. *Tyrophagus putrescentiae*.

It is a further object of the present invention to disclose the rearing composition as defined in any of the above, wherein said Astigmata prey population is in a frozen form.

It is a further object of the present invention to disclose the rearing composition as defined in any of the above, wherein said Astigmata prey population comprises a mixture comprising non-viable frozen developmental stages of juvenile mites.

It is a further object of the present invention to disclose the rearing composition as defined in any of the above, wherein said composition comprises at least one mite species of the genus *Phytoseiulus* and a mixture comprising non-viable frozen developmental stages of *C. lactis* juvenile mites and sawdust or another carrier material.

It is a further object of the present invention to disclose the rearing composition as defined in any of the above, wherein said composition comprises *P. persimilis* and a mixture comprising non-viable frozen developmental stages of *C. lactis* juvenile mites and sawdust or another carrier material.

It is a further object of the present invention to disclose the rearing composition as defined in any of the above, wherein said Astigmata prey population comprises non-viable *C. lactis* eggs.

It is a further object of the present invention to disclose the rearing composition as defined in any of the above, wherein said Astigmata prey population comprises non-viable eggs and non-viable juvenile mites in a 1:1 ratio (w/w).

It is a further object of the present invention to disclose the rearing composition as defined in any of the above, wherein said composition further comprises a carrier such as sawdust, bran or another carrier material.

It is a further object of the present invention to disclose the rearing composition as defined in any of the above, wherein said predator population reared on said mite species from the order Astigmata, is reproduced by an average rate of at least about 15% per day, particularly by a range of 15% to 25% per day.

It is a further object of the present invention to disclose the rearing composition as defined in any of the above, wherein said Astigmatid individuals are treated by a treatment selected from the group consisting of: thermal treatment, such as freezing, heating, cold-shock or heat-shock treatment; chemical treatment, such as gas or fume treatment; radiation treatment, such as UV, microwave, gamma irradiation or X-ray treatment; mechanical treatment, such as vigorous shaking, or stirring, subjecting to shear forces, collision; gas pressure treatment, such as ultrasound treatment, pressure changes, pressure drops; electrical treatment, such as electrocution; immobilizing with an adhesive; immobilization by starvation, such as induced by water or food deprivation; immobilization by suffocation or anoxia treatment, such as by temporarily eliminating oxygen from the atmosphere or replacing oxygen by another gas and any combination thereof.

It is a further object of the present invention to disclose the rearing composition as defined in any of the above, wherein said composition comprises *P. persimilis*, and a mixture comprising non-viable *C. lactis* eggs and sawdust or another carrier material.

It is a further object of the present invention to disclose the rearing composition as defined in any of the above, wherein said composition comprises *P. persimilis*, and a mixture comprising non-viable *C. lactis* mites and sawdust or another carrier material.

It is a further object of the present invention to disclose the rearing composition as defined in any of the above, wherein said composition comprises a *Phytoseiulus persimilis* predatory mite population, and dead *C. lactis* individuals as a prey mite population, further wherein said *Phytoseiulus persimilis* predatory mite population has a daily reproduction rate in the range of about 1.15-1.2.

It is a further object of the present invention to disclose the rearing composition as defined in any of the above, wherein said composition comprises a *Phytoseiulus persimilis* predatory mite population and dead individuals of at least one species belonging to the Astigmata order selected from the group consisting of: *Carpoglyphus lactis, Lepidoglyphus destructor, Glycifagus domestics, Dermatophagoides farinae* and *Dermatophagoides pteronisinus*.

It is a further object of the present invention to disclose the rearing composition as defined in any of the above, wherein said prey mite population further comprises a mite species of the family Phytoseiidae.

It is a further object of the present invention to disclose the rearing composition as defined in any of the above, wherein said prey mite species of the family Phytoseiidae is non-viable.

It is a further object of the present invention to disclose the rearing composition as defined in any of the above, wherein said composition is capable of controlling a crop pest.

It is a further object of the present invention to disclose the rearing composition as defined in any of the above, wherein said crop pest is selected from the group of mite pests, particularly members of the Acari family Tetranychidae such as twospotted spider mite, more particularly spider mite species, especially *Tetranychus, Panonychus* and various other mite species.

It is a further object of the present invention to disclose the rearing composition as defined in any of the above, wherein said composition is capable of reducing said crop pest counts by at least 50%.

It is a further object of the present invention to disclose the rearing composition as defined in any of the above formulated for controlled release of said predatory mites on a crop plant.

It is a further object of the present invention to disclose the rearing composition as defined in any of the above contained in a container configured for controlled release of said predatory mites on a crop plant.

It is a further object of the present invention to disclose the rearing composition as defined in any of the above wherein said predatory mites are capable slowly and continuously released from said container to said crop during a period of about three weeks.

It is a further object of the present invention to disclose a method for rearing predatory mite population comprising at least one mite species of the genus *Phytoseiulus*, the method comprising: (a) providing a composition as defined in any of the above; and (b) allowing individuals of the predatory mite population to prey on individuals of the Astigmatid population for at least 2 generations.

It is a further object of the present invention to disclose a method for rearing predatory mite population comprising at least one mite species of the genus *Phytoseiulus*, the method comprising: (a) providing a composition comprising a predatory mite population comprising at least one mite species of the genus *Phytoseiulus*, and a prey mite population comprising individuals of at least one mite species from the order Astigmata; (b) allowing individuals of the predatory mite population to prey on individuals of the Astigmatid population for at least 2 generations; wherein said Astigmata prey is selected from the group consisting of non-viable mites, non-viable eggs and a combination thereof.

It is a further object of the present invention to disclose the method as defined in any of the above, wherein the rearing population is maintained at a temperature range of 18-30° C., especially about 22° C.

It is a further object of the present invention to disclose the method as defined in any of the above, wherein the rearing population is maintained at a relative humidity of 70-90%, particularly about 85%.

It is a further object of the present invention to disclose the method as defined in any of the above, wherein said predatory mite is capable of oviposition for at least 2 generations, preferably for at least 10 generations, reared upon said Astigmata prey individuals.

It is a further object of the present invention to disclose the method as defined in any of the above, wherein said predatory mite population has a daily reproduction rate in the range of about 1.15-1.2.

It is a further object of the present invention to disclose the method as defined in any of the above, wherein said predatory mite population is characterized by a beige-white color.

It is a further object of the present invention to disclose the method as defined in any of the above, wherein said composition is absent of a fungus reducing agent.

It is a further object of the present invention to disclose the method as defined in any of the above, wherein said predatory mite species is selected from the group consisting of *Phytoseiulus fragariae, Phytoseiulus longipes, Phytoseiulus macropilis, Phytoseiulus persimilis* and *Phytoseiulus robertsi*.

It is a further object of the present invention to disclose the method as defined in any of the above, wherein said predatory mite species is *Phytoseiulus persimilis*.

It is a further object of the present invention to disclose the method as defined in any of the above, wherein the species from the order Astigmata is belonging to a family selected from the group consisting of Carpoglyphidae, Pyroglyphidae, Acaridae and Glycyphagidae.

It is a further object of the present invention to disclose the method as defined in any of the above, wherein the species from the order Astigmata comprises members from the family Carpoglyphidae, such as the genus *Carpoglyphus*, e.g. *Carpoglyphus lactis, Carpoglyphus munroi*; from the family Glycyphagidae such as the genus *Glycyphagus*, e.g. *Glycyphagus domesticus*, from the genus *Lepidoglyphus*, e.g. *Lepidoglyphus destructor*; from the family Pyroglyphidae such as the genus *Dermatophagoides*, e.g. *Dermatophagoides farinae, Dermatophagoides pteronisinus*, form the family Acaridae, such as the genus *Tyrophagus*, e.g. *Tyrophagus putrescentiae*.

It is a further object of the present invention to disclose the method as defined in any of the above, wherein said Astigmata prey population is in a frozen form.

It is a further object of the present invention to disclose the method as defined in any of the above, wherein said Astigmata prey population comprises a mixture comprising non-viable frozen developmental stages of juvenile mites.

It is a further object of the present invention to disclose the method as defined in any of the above, wherein said composition comprises at least one mite species of the genus *Phytoseiulus* and a mixture comprising non-viable frozen developmental stages of *C. lactis* juvenile mites and sawdust or another carrier material.

It is a further object of the present invention to disclose the method as defined in any of the above, wherein said composition comprises *P. persimilis* and a mixture comprising non-viable frozen developmental stages of *C. lactis* juvenile mites and sawdust or another carrier material.

It is a further object of the present invention to disclose the method as defined in any of the above, wherein said Astigmata prey population comprises non-viable *C. lactis* eggs.

It is a further object of the present invention to disclose the method as defined in any of the above, wherein said Astigmata prey population comprises non-viable eggs and non-viable juvenile mites in a 1:1 ratio (w/w).

It is a further object of the present invention to disclose the method as defined in any of the above, wherein said composition further comprises a carrier such as sawdust, bran or another carrier material.

It is a further object of the present invention to disclose the method as defined in any of the above, wherein said predator population reared on said mite species from the order Astigmata, is reproduced by an average rate of at least about 15% per day, particularly by a range of 15% to 25% per day.

It is a further object of the present invention to disclose the method as defined in any of the above, wherein said Astigmatid individuals are treated by a treatment selected from the group consisting of: thermal treatment, such as freezing, heating, cold-shock or heat-shock treatment; chemical treatment, such as gas or fume treatment; radiation treatment, such as UV, microwave, gamma irradiation or X-ray treatment; mechanical treatment, such as vigorous shaking, or stirring, subjecting to shear forces, collision; gas pressure treatment, such as ultrasound treatment, pressure changes, pressure drops; electrical treatment, such as electrocution; immobilizing with an adhesive; immobilization by starvation, such as induced by water or food deprivation; immobilization by suffocation or anoxia treatment, such as by temporarily eliminating oxygen from the atmosphere or replacing oxygen by another gas and any combination thereof.

It is a further object of the present invention to disclose the method as defined in any of the above, wherein said composition comprises *P. persimilis*, and a mixture comprising non-viable *C. lactis* eggs and sawdust or another carrier material.

It is a further object of the present invention to disclose the method as defined in any of the above, wherein said composition comprises *P. persimilis*, and a mixture comprising non-viable *C. lactis* mites and sawdust or another carrier material.

It is a further object of the present invention to disclose the method as defined in any of the above, wherein said composition comprises a *Phytoseiulus persimilis* predatory mite population, and dead *C. lactis* individuals as a prey mite population, further wherein said *Phytoseiulus persimilis* predatory mite population has a daily reproduction rate in the range of about 1.15-1.2.

It is a further object of the present invention to disclose the method as defined in any of the above, wherein said composition comprises a *Phytoseiulus persimilis* predatory mite population and dead individuals of at least one species belonging to the Astigmata order selected from the group consisting of: *Carpoglyphus lactis, Lepidoglyphus destructor, Glycifagus domestics, Dermatophagoides farinae* and *Dermatophagoides pteronisinus*.

It is a further object of the present invention to disclose the method as defined in any of the above, wherein said prey mite population further comprises a mite species of the family Phytoseiidae.

It is a further object of the present invention to disclose the method as defined in any of the above, wherein said prey mite species of the family Phytoseiidae is non-viable.

It is a further object of the present invention to disclose a method for controlling a crop pest, the method comprising applying a composition as defined in any of the above to a field crop.

It is a further object of the present invention to disclose the method as defined in any of the above, wherein said crop pest is selected from the group of mite pests, particularly members of the Acari family Tetranychidae such as twospotted spider mite, more particularly spider mite species, especially *Tetranychus, Panonychus* and various other mite species.

It is a further object of the present invention to disclose the use of the composition as defined in any of the above for controlling a crop pest.

It is a further object of the present invention to disclose the use as defined in any of the above, wherein the crop pest is selected from a range of mite pests, particularly members of the Acari family Tetranychidae such as twospotted spider mite, more particularly spider mite species, especially *Tetranychus, Panonychus* and various other mite species.

It is a further object of the present invention to disclose the use as defined in any of the above, wherein the crop is selected from the group consisting of greenhouse grown crops, open field crops, vegetables, ornamentals, fruit trees, hops, cotton and strawberries.

It is a further object of the present invention to disclose a biological control agent (BCA) for controlling crop pests comprising a mixture of (a) at least one predatory mite species of the genus *Phytoseiulus* raised by the composition as defined in any of the above, (b) optionally, prey mite individuals comprising at least one species from the order Astigmata, said Astigmata individuals are selected from the group consisting of non-viable mites, non-living eggs and a combination thereof; and (c) optionally a carrier material.

It is a further object of the present invention to disclose the BCA as defined in any of the above, wherein said predatory mite population is characterized by a beige-white color.

It is a further object of the present invention to disclose a container containing the composition as defined in any of the above, said container configured to be hung on a crop plant, said container comprises an exit hole from which said predatory mites are slowly and continuously released to said crop during a period of about three weeks.

It is a further object of the present invention to disclose the container as defined in any of the above, wherein said container is selected from the group consisting of a sachet, a packet, a pouch, a pocket, a sack, a bottle and a bag.

It is a further object of the present invention to disclose the container as defined in any of the above, wherein said prey mites are in a frozen form.

It is a further object of the present invention to disclose the container as defined in any of the above, wherein said prey mites are frozen Astigmatid mite eggs.

It is a further object of the present invention to disclose the container as defined in any of the above, wherein said prey mites are frozen eggs of *Carpoglyphus lactis*.

It is a further object of the present invention to disclose the rearing composition as defined in any of the above, wherein at least partially of the Astigmata prey population is immobilized.

It is a further object of the present invention to disclose the rearing composition as defined in any of the above, wherein the Astigmata prey population is immobilized.

It is a further object of the present invention to disclose the rearing composition as defined in any of the above, wherein the Astigmata prey population comprises dead eggs and at least partially immobilized mites.

It is a further object of the present invention to disclose the rearing composition as defined in any of the above, wherein the Astigmata prey population comprises eggs and dead mites.

It is a further object of the present invention to disclose the rearing composition as defined in any of the above, wherein the Astigmata prey population comprises eggs and immobilized juvenile mites in a 1:1 ratio (w/w).

It is a further object of the present invention to disclose the rearing composition as defined in any of the above, wherein the mites are immobilized by an immobilization treatment selected from the group consisting of: thermal treatment, such as freezing, heating, cold-shock or heat-shock treatment; chemical treatment, such as gas or fume treatment; radiation treatment, such as UV, microwave, gamma irradiation or X-ray treatment; mechanical treatment, such as vigorous shaking, or stirring, subjecting to shear forces, collision; gas pressure treatment, such as ultrasound treatment, pressure changes, pressure drops; electrical treatment, such as electrocution; immobilizing with an adhesive; immobilization by starvation, such as induced by water or food deprivation; immobilization by suffocation or anoxia treatment, such as by temporarily eliminating oxygen from the atmosphere or replacing oxygen by another gas and any combination thereof.

It is a further object of the present invention to disclose the rearing composition as defined in any of the above, wherein the composition comprises *P. persimilis*, and a mixture comprising immobilized *C. lactis* and sawdust or another carrier material. It is a further object of the present invention to disclose the rearing composition as defined in any of the above, wherein the immobilized *C. lactis* mites are dead mites.

It is a further object of the present invention to disclose the rearing composition as defined in any of the above, wherein the composition comprises a *Phytoseiulus persimilis* predatory mite population, and dead *C. lactis* individuals as a prey mite population, further wherein the *Phytoseiulus persimilis* predatory mite population is capable of oviposition for at least 2 generations, preferably for at least 10 generations. It is a further object of the present invention to disclose the rearing composition as defined in any of the above, wherein the composition comprises a *Phytoseiulus persimilis* predatory mite population and dead individuals of at least one species belonging to the Astigmata order selected from the group consisting of: *Carpoglyphus lactis, Lepidoglyphus destructor, Glycifagus domestics, Dermatophagoides farinae* and *Dermatophagoides pteronisinus*.

It is a further object of the present invention to disclose the rearing composition as defined in any of the above, wherein the prey mite population further comprises a mite species of the family Phytoseiidae.

It is a further object of the present invention to disclose the rearing composition as defined in any of the above, wherein the Phytoseiidae prey mite species is of the genus *Amblyseius*, e.g. *Amblyseius swirskii*.

It is a further object of the present invention to disclose the rearing composition as defined in any of the above, wherein the prey mite species is *Amblyseius swirskii*.

It is a further object of the present invention to disclose the rearing composition as defined in any of the above, wherein the composition comprises a *Phytoseiulus persimilis* predatory mite population and prey mite population comprising *Amblyseius swirskii* mite species.

It is a further object of the present invention to disclose the rearing composition as defined in any of the above, wherein the *Amblyseius swirskii* mites are at least partially immobilized.

It is a further object of the present invention to disclose a rearing composition comprising: predatory mite population comprising at least one mite species of the genus *Phytoseiulus*, and a prey mite population comprising at least one species from the Phytoseiidae family.

It is a further object of the present invention to disclose the rearing composition as defined in any of the above, wherein the prey mite species is of the genus *Amblyseius*, e.g. *Amblyseius swirskii*.

It is a further object of the present invention to disclose the rearing composition as defined in any of the above, wherein the prey mite is immobilized.

It is a further object of the present invention to disclose the method as defined in any of the above, wherein at least partially of the Astigmata prey population is immobilized.

It is a further object of the present invention to disclose the method as defined in any of the above, wherein the Astigmata prey population is immobilized.

It is a further object of the present invention to disclose the method as defined in any of the above, wherein the Astigmata prey population comprises a mixture comprising dead frozen developmental stages of juvenile mites.

It is a further object of the present invention to disclose the method as defined in any of the above, wherein the composition comprises *P. persimilis*, and a mixture comprising dead frozen developmental stages of *C. lactis* juvenile mites and sawdust or another carrier material.

It is a further object of the present invention to disclose the method as defined in any of the above, wherein the Astigmata prey population comprises eggs and at least partially immobilized mites.

It is a further object of the present invention to disclose the method as defined in any of the above, wherein the Astigmata prey population comprises eggs and dead mites.

It is a further object of the present invention to disclose the method as defined in any of the above, wherein the Astigmata prey population comprises eggs and immobilized juvenile mites in a 1:1 ratio (w/w).

It is a further object of the present invention to disclose the method as defined in any of the above, wherein the mites are immobilized by an immobilization treatment selected from the group consisting of: thermal treatment, such as freezing, heating, cold-shock or heat-shock treatment; chemical treatment, such as gas or fume treatment; radiation treatment, such as UV, microwave, gamma irradiation or X-ray treatment; mechanical treatment, such as vigorous shaking, or stirring, subjecting to shear forces, collision; gas pressure treatment, such as ultrasound treatment, pressure changes, pressure drops; electrical treatment, such as electrocution; immobilizing with an adhesive; immobilization by starvation, such as induced by water or food deprivation; immobilization by suffocation or anoxia treatment, such as by temporarily eliminating oxygen from the atmosphere or replacing oxygen by another gas and any combination thereof.

It is a further object of the present invention to disclose the method as defined in any of the above, wherein the composition comprises *P. persimilis*, and a mixture comprising immobilized *C. lactis* and sawdust or another carrier material.

It is a further object of the present invention to disclose the method as defined in any of the above, wherein the immobilized *C. lactis* mites are dead mites.

It is a further object of the present invention to disclose the method as defined in any of the above, wherein the composition comprises a *Phytoseiulus persimilis* predatory mite population, and dead *C. lactis* individuals as a prey mite population, further wherein the *Phytoseiulus persimilis* predatory mite population is capable of oviposition for at least 2 generations, preferably for at least 10 generations.

It is a further object of the present invention to disclose the method as defined in any of the above, wherein the composition comprises a *Phytoseiulus persimilis* predatory mite population and dead individuals of at least one species belonging to the Astigmata order selected from the group consisting of: *Carpoglyphus lactis, Lepidoglyphus destructor, Glycifagus domestics, Dermatophagoides farinae* and *Dermatophagoides pteronisinus*.

It is a further object of the present invention to disclose the method as defined in any of the above, wherein the prey mite population further comprises a mite species of the family Phytoseiidae.

It is a further object of the present invention to disclose the method as defined in any of the above, wherein the prey mite species is of the genus *Amblyseius*, e.g. *Amblyseius swirskii*.

It is a further object of the present invention to disclose the method as defined in any of the above, wherein the prey mite species is *Amblyseius swirskii*.

It is a further object of the present invention to disclose the method as defined in any of the above, wherein the composition comprises a *Phytoseiulus persimilis* predatory mite population and prey mite population comprising *Amblyseius swirskii* mite species.

It is a further object of the present invention to disclose the method as defined in any of the above, wherein the *Amblyseius swirskii* mites are at least partially immobilized.

It is a further object of the present invention to disclose a method for rearing predatory mite population comprising at least one mite species of the genus *Phytoseiulus*, the method comprising: (a) providing a rearing composition comprising: a predatory mite population comprising at least one mite species of the genus *Phytoseiulus*, and a prey mite population comprising individuals of at least one mite species from the order Astigmata, wherein said predatory mite population is capable of oviposition for at least 2 generations, further wherein said Astigmata prey is selected from the group consisting of non-viable mites, non-viable eggs and a combination thereof, wherein said composition is capable of controlling a crop pest; and (b) allowing individuals of the predatory mite population to prey on individuals of the Phytoseiidae family population.

It is a further object of the present invention to disclose the method as defined in above, wherein the predatory mite species is selected from the group consisting of *Phytoseiulus fragariae, Phytoseiulus longipes, Phytoseiulus macropilis, Phytoseiulus persimilis* and *Phytoseiulus robertsi*.

It is a further object of the present invention to disclose the method as defined in any of the above, wherein the predatory mite species is *Phytoseiulus persimilis*.

It is a further object of the present invention to disclose the method as defined in any of the above, wherein the prey mite species is of the genus *Amblyseius*, e.g. *Amblyseius swirskii*.

It is a further object of the present invention to disclose the method as defined in any of the above, wherein the prey mite is immobilized.

It is a further object of the present invention to disclose a biological control product for controlling crop pests comprising a mixture of (a) *Phytoseiulus persimilis* predatory mite individuals raised by the composition as defined in any of the above, (b) prey mite individuals comprising at least one species from the order Astigmata, and (c) optionally a carrier material.

It is a further object of the present invention to disclose the biological control product as defined above, wherein the species from the order Astigmata comprises members from the family Carpoglyphidae, such as the genus *Carpoglyphus*, e.g. *Carpoglyphus lactis, Carpoglyphus munroi*; from the family Glycyphagidae such as the genus *Glycyphagus*, e.g. *Glycyphagus domesticus*, from the genus *Lepidoglyphus*, e.g. *Lepidoglyphus destructor*; from the family Pyroglyphidae such as the genus *Dermatophagoides*, e.g. *Dermatophagoides farinae, Dermatophagoides pteronisinus*, from the family Acaridae, such as the genus *Tyrophagus*, e.g. *Tyrophagus putrescentiae*.

It is a further object of the present invention to disclose a biological control product for controlling crop pests comprising a mixture of (a) *Phytoseiulus persimilis* predatory mite individuals raised by the composition as defined in any of the above, (b) prey mite individuals comprising at least one species from the Phytoseiidae family, and (c) optionally a carrier material.

It is a further object of the present invention to disclose a biological control product for controlling crop pests comprising predatory mite individuals of the genus *Phytoseiulus* raised by the composition as defined in any of the above.

It is a further object of the present invention to disclose the composition as defined in any of the above, formulated for controlled release of the predatory mites on a crop plant.

It is a further object of the present invention to disclose a container containing the composition as defined in any of the above, the container configured to be hung on a crop plant, the container comprises an exit hole from which the predatory mites are slowly and continuously released to the crop during a period of about three weeks.

It is a further object of the present invention to disclose the container as defined above, wherein the container is selected from the group consisting of a sachet, packet, pouch, pocket, sack and a bag.

It is a further object of the present invention to disclose the container as defined in any of the above, wherein the prey mites are frozen astigmatid mite eggs.

It is a further object of the present invention to disclose the container as defined in any of the above, wherein the prey mites are frozen eggs of *Carpoglyphus lactis*.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings; wherein.

DETAILED DESCRIPTION OF THE INVENTION

Figure 1:
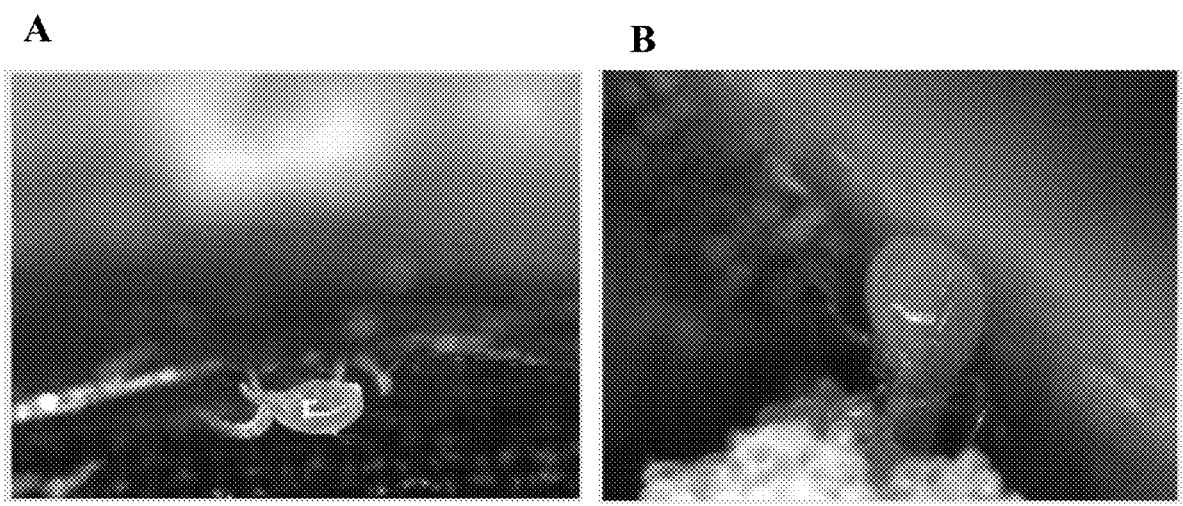
FIG. 1 is a photographic illustration of different developmental stages of *P. persimilis* reared on dead or immobilized *Carpoglyphus lactis* (*C. lactis*) mites.

The twospotted spider mite, *Tetranychus urticae* Koch, is the major spider mite pest of ornamental plants and vegetable crops grown in greenhouses. Furthermore, this ubiquitous spider mite is a serious pest of numerous ornamental plants in home landscapes and is of considerable importance as a pest of food and fiber crops throughout the world (van de Vrie et al., 1972). The predacious phytoseiid mite *Phytoseiulus persimilis* is the major species used to control twospotted spider mites in greenhouse as well as open field crops.

*Phytoseiulus persimilis* is a predatory mite which specializes on a diet of spider mites. Spider mites are vegetarian mites (phytophagous mites) and therefore require rearing on plants, which is undesirable since it involves complex operations and high rearing costs.

The present invention provides for the first time alternative method for rearing *P. persimilis* and other mite species of the genus *Phytoseiulus*. The current invention shows, against the conventional thinking, that mite species of the genus *Phytoseiulus*, e.g. *P. persimilis*, could broaden its dietary range, and could be reared on other preys, which are cheaper to produce and therefore much more desirable. The alternative prey mites are mostly Astigmatic mites that feed on stored products and are therefore significantly cheaper to produce.

According to one embodiment, the present invention provides a system and method for using mites (especially dead mites) of the species *Carpoglyphus lactis* (Cl) or other Astigmatic mite as an alternative food for mite species of the *Phytoseiulus* genus, such as *Phytoseiulus persimilis*.

It is shown by the present invention that mite species of the genus *Phytoseiulus*, especially *Phytoseiulus persimilis*, can complete its life cycle and reproduce when feeding on dead mites belonging to the order Astigmata (within the Arachnida class).

The present invention is aimed at developing a system for the production of mite species of the genus *Phytoseiulus*, e.g. *Phytoseiulus persimilis*, on a diet comprising Astigmatic mites. The system is based on the following components:

1. The predator—specifically *Phytoseiulus persimilis* and more generally mites of the genus *Phytoseiulus*.
2. The prey—a mite species, possibly *Carpoglyphus lactis, Glyciphagus domesticus, Lepidoglyphus destructor, Dermatophagoides farinae, Dermatophagoides pteronisinus* or other Astigmatic mite, or other mite species such as *Amblyseius swirskii*.
3. The rearing system—the specific setup in which the mites are reared, comprising the rearing media, the way the prey mite is presented to the predator, the prey developmental stage and other factors.

The following rearing methods are within the scope of the present invention:

1. The predator is reared on a living mixture of prey mites.
2. The predator receives a mixture of immobilized prey mites by means of freezing or by other means such as irradiation.
3. A certain developmental stage of the prey mite is extracted from the prey mite's population, and then served alive or dead as food to the predator.

It is noted that in all of the above optional rearing methods, the prey mite could be either the above mentioned Astigmatic mites, or other species.

With respect to the final biological control product, the following is within the scope of the present invention:

1. A mixture which contains both the predator and the prey mites, or the predator and specific stages of the prey mites used for feeding the predator.
2. A further option is extracting only the predators, so that the final product contains only the predators.

According to one embodiment, the present invention provides a rearing composition comprising: a predatory mite population comprising at least one mite species of the genus *Phytoseiulus*, and a prey mite population comprising individuals of at least one mite species from the order Astigmata, wherein said predatory mite population is capable of oviposition for at least 2 generations, further wherein said Astigmata prey is selected from the group consisting of non-viable mites, non-viable eggs and a combination thereof.

It is within the scope of the present invention that the predatory mite is capable of oviposition for at least 10 generations and preferably more, having the Astigmata individuals as a prey.

It is further within the scope that the predatory mite population exhibits an increased reproduction rate trait as compared to a control predatory mite population, of the same species, lacking the aforementioned trait.

It is further within the scope that the predatory mite population of the present invention exhibits a daily reproduction rate in the range of about 1.15-1.2.

It is further within the scope of the present invention that the predatory mite population is characterized by a beige-white color, when said *Phytoseiulus* predatory mite is reared upon said Astigmata prey as a food source.

It is within the scope of the present invention that the predators would have a different appearance than that of the common product containing *P. persimilis* mites reared on spider mites (white mites in the case of the present invention instead of the usual orange).

According to a further embodiment, the present invention shows for the first time that a population of *P. persimilis* successfully developed and reproduced on dead *Carpoglyphus lactis* for at least six months (about 25 generations).

It is emphasized that *P. persimilis* is herein surprisingly reported to complete its life cycle and reproduce on either non-phytophagous prey (prey that doesn't require to feed on living plants), or prey that doesn't consume phytophagous mites.

The present invention provides a mite composition which contains a *Phytoseiulus persimilis* rearing mite population, and a factitious host mite population comprising at least one species from the order Astigmata or from the family Phytoseiidae. Up until now, mite species of the genus *Phytoseiulus*, such as the important predator mite *Phytoseiulus persimilis*, were reared on their natural phytophagous mite diet which involves high costs and resources (such as providing appropriate plants in sufficient abundance, under greenhouse conditions).

The present invention solves the serious problem of rearing the main spider-mite controlling predator, *Phytoseiulus persimilis*, by rearing it in a cost effective and efficient way on a non-phytophagous alternative diet.

Accordingly, the invention provides a mite composition comprising: a rearing population of mite species of the genus *Phytoseiulus*, for example *Phytoseiulus persimilis* predatory mite species, a population of at least one species from the order Astigmata or from the family Phytoseiidae, and optionally a carrier.

According to one embodiment, the present invention provides a rearing composition comprising: predatory mite population comprising at least one mite species of the genus *Phytoseiulus*, and a prey mite population comprising at least one species from the order Astigmata.

According to a further embodiment, the present invention provides a method for rearing predatory mite population comprising at least one mite species of the genus *Phytoseiulus*, the method comprising: (a) providing a composition comprising a predatory mite population comprising at least one mite species of the genus *Phytoseiulus*, and a prey mite population comprising at least one species from the order Astigmata; and (b) allowing individuals of the predatory mite population to prey on individuals of the Astigmatid population.

According to a further embodiment, the present invention provides a rearing composition comprising: predatory mite population comprising at least one mite species of the genus *Phytoseiulus*, and a prey mite population comprising at least one species from the Phytoseiidae family.

According to a further embodiment, the present invention provides a method for rearing predatory mite population comprising at least one mite species of the genus *Phytoseiulus*, the method comprising: (a) providing a composition comprising: predatory mite population comprising at least one mite species of the genus *Phytoseiulus*, and a prey mite population comprising at least one species from the Phytoseiidae family; and (b) allowing individuals of the predatory mite population to prey on individuals of the Phytoseiidae family population.

In some embodiments, the prey population i.e. species from the order Astigmata or species from the Phytoseiidae family, is immobilized and/or not alive.

It is further within the scope that the *Phytoseiulus persimilis* predatory mite is capable of reproducing for at least 2 generations, preferably at least 10 generations, more preferably for at least 15 generations or more generations, feeding on the aforementioned Astigmata population.

The composition of the present invention provides a considerable number of advantages over previous combinations. In one aspect, the food material used to feed the prey during predator production will no longer be plants or phytophagous mites, but mites that live upon stored products, therefore providing a substantial cost saving.

In another aspect, the present invention provides a rearing composition comprising: predatory mite population comprising at least one mite species of the genus *Phytoseiulus*, and a prey mite population comprising at least one species from the Phytoseiidae family.

According to some further embodiments of the present invention, the predatory mite species is selected from the group consisting of *Phytoseiulus fragariae, Phytoseiulus longipes, Phytoseiulus macropilis, Phytoseiulus persimilis* and *Phytoseiulus robertsi*.

According to further embodiments of the present invention, the predatory mite species is *Phytoseiulus persimilis*.

According to yet further embodiments of the present invention, the prey mite species is of the genus *Amblyseius*, e.g. *Amblyseius swirskii*.

According to further embodiments of the present invention, the rearing composition comprises immobilized prey mites.

According to further aspects of the present invention, the prey mites are immobilized or dead mites.

According to further aspects, the present invention provides a method for controlling a crop pest, the method comprising applying a composition as defined in any of the above to a field crop.

According to further aspects, the present invention provides use of the composition as defined in any of the above for controlling a crop pest.

According to further aspects, the present invention provides a biological control product for controlling crop pests comprising a mixture of (a) *Phytoseiulus persimilis* predatory mite individuals raised by the composition as defined in any of the above, (b) prey mite individuals comprising at least one species from the order Astigmata, and (c) optionally a carrier material.

According to further aspects, the present invention provides a biological control product for controlling crop pests comprising a mixture of (a) *Phytoseiulus persimilis* predatory mite individuals raised by the composition as defined in any of the above, and (b) prey mite individuals comprising at least one species from the Phytoseiidae family, and (c) optionally a carrier material.

The present invention further provides a slow release system (e.g. sachet) for mites, especially for mite species of the genus *Phytoseiulus*, particularly *Phytoseiulus persimilis* (*P. persimilis*) configured to be applied on a crop.

A core aspect of the innovative solution is that the predatory mites can reproduce within the system for several generations, while a certain proportion of the predatory mites continuously leaves the system and reaches the crop to control pests. This provides a continuous supply of mites to the crop without the need to apply them repeatedly by the farmer.

Embodiments of the slow release system provided by the present invention are based upon the following features:
1. Predatory mite individuals—*P. persimilis* or other mite species of the *Phytoseiulus* genus.
2. Food source for the predatory mites—a factitious prey or host for example, frozen eggs of *Carpoglyphus lactis* (*C. lactis*) or another astigmatic mite.
3. The predatory mites are combined with their factitious host at the same physical location. This is done by the following alternative approaches:
   a. Providing the predatory mites with their factitious host in a container such as a sachet, packet, pouch, pocket, sack or a bag configured to be hung on the crop plant, from which the mites would slowly and continuously be released to the crop during a period of about three weeks.
   b. Applying a mixture containing the predatory mites, a carrier and the factitious host as a food source, directly on the crop leaves. From this mixture, the predatory mites would slowly be released to the crop during a period of about three weeks.

It is noted that such slow release systems for predatory mites are highly desirable for *P. persimilis* since up until now, *P. persimilis* was known as a specialist (natural enemy) of spider mites and therefore reared upon spider mites diet. However, spider mites are not suitable to be used in this kind of mite release systems for crop protection for the following reasons:

Spider mites are pests themselves, and if applied alive, they may damage the crop.

Spider mites cannot reproduce without being supplied with plant material, therefore can't reproduce in a sachet.

Without being supplied with a food source, living spider mites die rapidly and shrivel (e.g. within few days).

If served dead, spider mites quickly shrivel and loose their nutritional value.

Spider mites are expensive to produce.

The present invention provides an unexpected technological solution for the above problem, which was not shown to be successful up until now. The solution is based upon using frozen eggs of *C. lactis* or other astigmatid mite species as a factitious host for *P. persimilis*. Contrary to spider mites, frozen eggs of *C. lactis* maintain their nutritional value for about three weeks. This innovative solution enables the prolonged release of *P. persimilis* predatory mites from a container or a mixture combining the predatory mite with its factitious host, applied directly on the crop plant for controlling pests.

As used herein the term "about" denotes ±10% of the defined amount or measure or value.

The term "controlled release" refers hereinafter to slow release, sustained-release, rapid release, designed to release in a prolonged controlled mode or fashion. In the context of the present invention, it refers to predatory mite release to the crop plant gradually over a specified period of time, e.g. throughout the day or over a week.

The term "slow release system" or a "container" refers herein after to a sachet-type release system, e.g. a sachet, packet, pouch, pocket, sack, a bottle or a bag which contains the composition or formulation of the present invention of *Phytoseiulus* predatory mites, a factitious host (dead astigmatid mites) and optionally a carrier. It is further included within the scope of the present invention that such a system or container refers to an apparatus, a unit, a device, a compartment, a member, strip or housing for slow release of beneficial insects or predatory mites available or known in the art.

It is also within the scope of the present invention that the *Phytoseiulus* predatory mite releasing system may be of any suitable type. In general the mite releasing system may comprise a container suitable for holding the individuals of the *Phytoseiulus* predatory mite (e.g. *P. persimilis*) and individuals of the factitious host mite (e.g. dead *C. lactis* eggs). The container comprises an opening and/or means for generating an exit opening for mobile stages of the *Phytoseiulus* predatory mite. Releasing systems of this type are known to the skilled person and various products are commercially available on the market, e.g. sachet-type releasing systems and other suitable types of releasing systems which are included within the scope of the present invention.

The term "rearing composition" as used herein generally refers to a composition suitable for breeding, bringing up, raising, upbringing or propagating a mite species. More specifically, it refers to a composition suitable for the commercial rearing of mites. It is herein acknowledged that mass rearing systems for predatory mites heavily depend on the availability of suitable prey for the predators. Therefore, there is a continuing need to improve rearing systems of both predatory mites and mites suitable as rearing prey. To solve this problem, the present invention provides a composition or system specifically adapted for effectively and efficiently rearing mite species of the genus *Phytoseiulus*, especially *Phytoseiulus persimilis*, a highly important predatory mite used for crop pest (spider mites) biological control. For the first time, *Phytoseiulus persimilis* is shown to complete its life cycle and reproduce, i.e. for at least 2 generations, by being reared on Astigmatid mite species or on Phytoseiidae prey mite species, e.g. *Amblyseius swirskii*.

The term "carrier" refers hereinafter to an inactive or inert substance or particles or vehicle. In a preferred embodiment the rearing composition of the present invention comprises a carrier for the individuals of the mite species. The carrier can be any solid material which is suitable to provide a carrier surface to the mite individuals. Examples of suitable carriers are plant materials such as bran (e.g. wheat), sawdust (e.g. fine sawdust), corn cob grits, vermiculite, etc.

The term "*Phytoseiulus*" as used hereinafter refers to a genus of mites in the Phytoseiidae family. This genus of predatory mites is most frequently used to control two-spotted spider mites in greenhouses and outdoor crops. It is within the scope of the present invention that the genus *Phytoseiulus* contains the following species: *Phytoseiulus fragariae, Phytoseiulus longipes, Phytoseiulus macropilis, Phytoseiulus persimilis* and *Phytoseiulus robertsi*. The *Phy-*

*toseiulus* predetoy mites are known as specialists for spider mites (mites of the family Tetranychidae) which are phytophagous mites.

The term "*Phytoseiulus persimilis*" or "*P. persimilis*" as used hereinafter refers to a predatory mite population comprising the *Phytoseiulus persimilis* (*P. persimilis*). *Phytoseiulus* is a genus of mites in the Phytoseiidae family. This predatory mite is the mite predator most frequently used to control two-spotted spider mites in greenhouses and outdoor crops grown in mild environments.

*P. persimilis* is generally used for spider mite control and management. They are voracious predators of most of the spider mite pests (*Tetranychus* spp). Some of the species they impact include: the two-spotted mite *Tetranychus urticae*, the carmine red mite *T. cinnabarinus*, and the Pacific mite *T. pacificus*. Unlike *Neoseiulus californicus* (Order: Mesostigmata, Family: Phytoseiidae, Subfamily: Amblyseiinae) which may not eat for relatively long periods, *Phytoseiulus persimilis* must have fresh feed. Furthermore, *Phytoseiulus persimilis* are not flexible by their diet as other available predatory mite species for spider mite control, since they are known to only feed upon specific *Tetranychus* species, but not all of them.

The present invention solves these problems by providing for the first time a composition for mass rearing *P. persimilis* which contains mite species of the order Astigmata. The rearing system of the present invention is much more cost effective than rearing *P. persimilis* on its conventional diet which consists of phytophagous mites.

The term "factitious host" generally refers hereinafter to an unnatural host or host other than the target host for the predatory mite, one that biocontrol practitioners may more readily rear than the target host in a laboratory. In the context of the present invention, factitious host or prey refers to organisms unlikely to be attacked by a natural enemy or predatory mite in its natural habitat, but that is artificially used to support its development and/or reproduction. Usually it is a species that is easier and less expensive to rear. Examples within the scope of the present invention include storage mites (such as astigmatid mites) for predatory mites (such as *Phytoseiulus* mite species), mite eggs for predatory insects and mites. According to further aspects, the term factitious host is used when a biological control agent is forced to feed on an insect or mite that it would not feed on it in nature. This can allow higher production levels. The present invention shows for the first time that species of commercially available *Phytoseiulus* mites can be mass reared using astigmatid mites (Acari: Astigmata) as factitious prey.

The term "juvenile mite" or "juvenile mites" refers hereinafter to mite developmental life stages or mite developmental phases or instar including egg, larva, protonymph and deutonymph (third instar) individuals.

The term "individual" or "individuals" or "mite individuals" refers in the context of the present invention to mite developmental stages including, but not limited to eggs, juvenile mite stages such as larva, protonymph and deutonymph (third instar) individuals.

The term "mobile stages" refers hereinafter to mite developmental stages including larva, protonymph, deutonymph (third instar) and adult stages.

The term "non-viable" used hereinafter generally means not capable of living, growing, developing, or functioning. According to main aspects of the present invention it refers to dead or not alive or non-living or immobilized mites (i.e. any mite developmental stage or phase) or mite eggs. In a specific embodiment of the present invention, non-viable Astigmata mites and/or eggs are used as a prey for predatory mites of the *Phytoseiulus* genus.

According to some embodiments of the present invention the non viable mites or eggs are produced by or exposed to a treatment including, but not limited to, thermal treatment, such as freezing, freeze-drying, heating, cold-shock or heat-shock treatment; chemical treatment, such as gas or fume treatment; radiation treatment, such as UV, microwave, gamma irradiation or X-ray treatment; mechanical treatment, such as vigorous shaking, or stirring, subjecting to shear forces, collision; gas pressure treatment, such as ultrasound treatment, pressure changes, pressure drops; electrical treatment, such as electrocution; immobilizing with an adhesive; immobilization by starvation, such as induced by water or food deprivation; immobilization by suffocation or anoxia treatment, such as by temporarily eliminating oxygen from the atmosphere or replacing oxygen by another gas and any combination thereof.

According to a specific embodiment, the composition of the present invention comprises dead frozen *C. lactis* eggs used as a prey for predatory mites of the *Phytoseiulus* genus. The term "Astigmatid" or "Astigmata" or "Astigmatic mites" or "Astigmatina" as used herein refers to mites order within the Subclass: Acari. The Astigmatina are a "cohort" of mites. Astigmatina belongs to the Sarcoptiformes, which contains the "biting" Acariformes. The Astigmata order contains superfamilies with over thousands of genera. Non limiting examples of such superfamilies and families, within the scope of the present invention may include:

Suborder: Acaridia
Superfamilies:
    Schizoglyphoidea: examples of families include: Schizoglyphidae
    Histiostomatoidea: examples of families include: Histiostomatidae, Guanolichidae
    Canestrinioidea: examples of families include: Chetochelacaridae, Lophonotacaridae, Canestriniidae, Heterocoptidae
    Hemisarcoptoidea: examples of families include: Chaetodactylidae, Hyadesiidae, Carpoglyphidae, Algophagidae, Hemisarcoptidae, Winterschmidtiidae
    Glycyphagoidea: examples of families include: Euglycyphagidae, Chortoglyphidae, Pedetropodidae, Echimyopodidae, Aeroglyphidae, Rosensteiniidae, Glycyphagidae
    Acaroidea: examples of families include: Sapracaridae, Suidasiidae, Lardoglyphidae, Glycacaridae, Gaudiellidae
    Acaridae: examples of families include: Hypoderoidea, Hypoderidae
Suborder: Psoroptidia
Superfamilies:
    Pterolichoidea: examples of families include: Oconnoriidae, Ptiloxenidae
    Pterolichidae: examples of families include: Cheylabididae, Ochrolichidae, Gabuciniidae, Falculiferidae, Eustathiidae, Crypturoptidae, Thoracosathesidae, Rectijanuidae, Ascouracaridae, Syringobiidae, Kiwilichidae, Kramerellidae
    Freyanoidea: examples of families include: Freyanidae, Vexillariidae, Caudiferidae
    Analgoidea: examples of families include: Heteropsoridae, Analgidae, Xolalgidae, Avenzoariidae, Pteronyssidae, Proctophyllodidae, Psoroptoididae, Trouessartiidae, Alloptidae, Thysanocercidae, Dermationidae, Epidermoptidae, Apionacaridae, Dermoglyphidae, Laminosioptidae, Knemidokoptidae, Cytoditidae Pyroglyphoidea: examples of families include: Pyroglyphidae, Turbinoptidae Psoroptoidea: examples of families include: Psoroptidae, Galagalgidae, Lobalgidae, Myocoptidae, Rhyncoptidae, Audycoptidae, Listrophoridae, Chirodiscidae, Atopomelidae, Chirorhynchobiidae, Gastronyssidae, Lemurnyssidae, Pneumocoptidae, Sarcoptidae A preferable Astigmatid mite species used by the biological control system of the present invention as a factitious host population for the *Phytoseiulus* predatory mite, e.g. *P. persimilis*, is a mite species of the Carpoglyphidae family, more preferably *Carpoglyphus lactis* (*C. lactis*).

Carpoglyphidae is a mite family in the order Astigmatina, containing four genera: *Carpoglyphus, Coproglyphus, Dichotomiopus* and *Pullea*.

*Carpoglyphus lactis* (*Acarus lactis*), preferably used by the present invention as a diet for rearing *P. persimilis*, belongs to the *Carpoglyphus* genera. *Carpoglyphus lactis* is acknowledged herein as a stored product mite, infesting saccharide-rich stored commodities including dried fruits, wine, beer, milk products, jams and honey. Since *C. lactis* is capable of feeding on stored products, it is highly desirable and cost effective to raise *P. persimilis* on this mite species, as shown for the first time by the present invention.

In a further embodiment of the present invention, the *Phytoseiulus* predatory mite, e.g. *P. persimilis*, can complete its life cycle and reproduce when feeding on dead mites of the species *Carpoglyphus lactis* and/or *Dermatophagoides farinae* both belonging to the Astigmata order.

The term "trait" refers hereinafter to characteristic or phenotype. A phenotypic trait may refer to the appearance or other detectable characteristic of an individual, resulting from the interaction of its genome, proteome and/or metabolome with the environment. For example, in the context of the present invention an increased reproduction rate as described herein is a phonotypical trait characterizing the predatory mites of the composition of the present invention. According to a further embodiment of the present invention, a trait may also arise from interaction between the mite and its associated microorganisms. A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; conventionally, a recessive trait manifests itself only when present at homozygous state.

The term "genetic linkage" is understood within the scope of the invention to refer to an association of characters in inheritance due to location of genes in proximity on the same chromosome, measured by percent recombination between loci (centi-Morgan, cM).

As used herein, the term "population" means a genetically heterogeneous collection of mites sharing a common genetic derivation.

As used herein, the phrase "genetic marker" or "molecular marker" or "biomarker" refers to a feature in an individual's genome e.g., a nucleotide or a polynucleotide sequence that is associated with one or more loci or trait of interest In some embodiments, a genetic marker is polymorphic in a population of interest, or the locus occupied by the polymorphism, depending on context. Genetic markers or molecular markers include, for example, single nucleotide polymorphisms (SNPs), indels (i.e. insertions deletions), simple sequence repeats (SSRs), restriction fragment length polymorphisms (RFLPs), random amplified polymorphic DNAs (RAFDs), cleaved amplified polymorphic sequence (CAPS) markers, Diversity Arrays Technology (DArT) markers, and amplified fragment length polymorphisms (AFLPs) or combinations thereof, among many other examples such as the DNA sequence per se. Genetic markers can, for example, be used to locate genetic loci containing alleles on a chromosome that contribute to variability of phenotypic traits. The phrase "genetic marker" or "molecular marker" or "biomarker" can also refer to a polynucleotide sequence complementary or corresponding to a genomic sequence, such as a sequence of a nucleic acid used as a probe or primer.

A genetic marker can be physically located in a position on a chromosome that is within or outside of the genetic locus with which it is associated (i.e., is intragenic or extragenic, respectively).

As used herein, the term "germplasm" refers to the totality of the genotypes of a population or other group of individuals (e.g., a species).

The terms "hybrid" and "hybrid progeny" used herein refers to an individual produced from genetically different parents (e.g., a genetically heterozygous or mostly heterozygous individual).

The term "allele(s)" used herein means any of one or more alternative or variant forms of a gene or a genetic unit at a particular locus, all of which alleles relate to one trait or characteristic at a specific locus. In a diploid cell of an organism, alleles of a given gene are located at a specific location, or locus (loci in plural) on a chromosome. One allele is present on each chromosome of the pair of homologous chromosomes. A diploid plant species may comprise a large number of different alleles at a particular locus. Such alternative or variant forms of alleles may be the result of single nucleotide polymorphisms, insertions, indels, inversions, translocations or deletions, or the consequence of gene regulation caused by, for example, by chemical or structural modification, transcription regulation or post-translational modification/regulation. An allele associated with a qualitative trait may comprise alternative or variant forms of various genetic units including those that are identical or associated with a single gene or multiple genes or their products or even a gene disrupting or controlled by a genetic factor contributing to the phenotype represented by the locus. As used herein, the term "locus" (loci in plural) means a specific place or places or region or a site on a chromosome where for example a gene or genetic marker element or factor is found. In specific embodiments, such a genetic element is contributing to a trait.

As used herein, the term "breeding" and grammatical variants thereof, refer to any process that generates a progeny individual. Breeding can be sexual or asexual, or any combination thereof. Exemplary non-limiting types of breeding include crossing, introgressing, selfing, backcrossing, doubled haploid derivative generation, and combinations thereof.

The term "genetic determinant" as used herein refers to genetic determinants such as genes, alleles, QTLs or traits.

Introgression of a genetic determinant means the incorporation of genes, alleles, QTLs or traits into a line wherein essentially all of the desired morphological and physiological characteristics of the line are recovered, in addition to the genetically introgressed determinant. Such a process is often used in cultivar development, in which one or a few genetic determinants are transferred to a desired genetic background, preferably by using backcrossing.

The term "genotype" refers to the genetic constitution of a cell or organism. An individual's genotype includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest. Thus, in some embodiments a genotype comprises a summary of one or more alleles present within an individual at one or more genetic loci. In some embodiments, a genotype is expressed in terms of a haplotype.

According to a further embodiment of the present invention, the *Phytoseiulus* predatory mite, e.g. *P. persimilis*, can complete its life cycle and reproduce (i.e. including development and oviposition) for at least 3 generations, when feeding on living juvenile mites of the species *Amblyseius swirskii* that belongs to the Phytoseiidae family.

It is further within the scope of the present invention to disclose a population of *Phytoseiulus* predatory mites, e.g. the mite species *P. persimilis*, reared by feeding on dead or immobilized mite species selected from the group comprising *Carpoglyphus lactis, Dermatophagoides farinae, Lepidogyphus destructor, Glyciphagus domesticus, Dermatophagoides pteronisinus, Amblyseius swirskii*, and any combination thereof.

According to a further embodiment, the predatory mite fed on the above prey mites, developed and reproduced for at least two generations.

According to a further embodiment of the present invention, *P. persimilis* or other *Phytoseiulus* predatory mite, can develop on dead individuals of the following species belonging to the Astigmata order: *Carpoglyphus lactis, Lepidoglyphus destructor, Glycifagus domesticus* and *Dermatophagoides pteronisinus*.

It is further within the scope that the mites used as prey are immobilized by immobilization treatment selected from the group consisting of: thermal treatment, such as freezing, heating, cold-shock or heat-shock treatment; chemical treatment, such as gas or fume treatment; radiation treatment, such as Gamma irradiation, UV, microwave or X-ray treatment; mechanical treatment, such as vigorous shaking, or stirring, subjecting to shear forces, collision; gas pressure treatment, such as ultrasound treatment, pressure changes, pressure drops; electrical treatment, such as electrocution; immobilizing with an adhesive; immobilization by starvation, such as induced by water or food deprivation; immobilization by suffocation or anoxia treatment, such as by temporarily eliminating oxygen from the atmosphere or replacing oxygen by another gas.

The skilled person will understand how these treatments may result in the immobilization of the Astigmatid individuals or other mites of the Phytoseiidae family and that the immobilization treatment should be such that the mite individuals remain a suitable prey (food source) for the predatory mite individuals.

It is further within the scope that the term "immobilized mites" may also mean dead or non-living mites.

Reference is now made to FIG. 1 photographically presenting different developmental stages of *P. persimilis* reared on dead or immobilized *C. lactis*. The figure presents an adult female (FIG. 1A) and a juvenile that had just hatched from the egg (FIG. 1B). As can be seen in this figure, all stages are characterized by a pale whitish color, typical to this diet, in contrast to the normal orange color obtained when feeding *P. persimilis* by spider mites, their conventional diet. In other words, the predators of the present invention, fed on *C. lactis*, turn to beige-white instead of the typical orange color. In addition, the dorsal shield of the predator is darker than the cuticle around it. This figure demonstrates that *P. persimilis* can develop and reproduce on dead or immobilized *C. lactis* mites. As explained above, *C. lactis* (Acari: Astigmata) are significantly more cost effective to produce than the conventional *P. persimilis* diet, which is the phytophagous spider mite.

Figure 2:
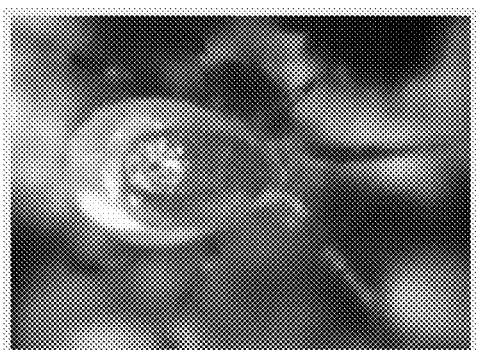
FIG. 2 is a photographic illustration of *P. persimilis* reared on dead or immobilized *Carpoglyphus lactis* (*C. lactis*) mites, as an embodiment of the present invention.

Reference is now made to FIG. 2 photographically presenting *P. persimilis* reared on dead or immobilized *C. lactis*. As can be seen, the predator has a unique appearance, where it turns to beige-white instead of the typical orange (when fed on conventional spider mite diet) and the dorsal shield of the predator is darker than the cuticle around it.

It is herein acknowledged that twospotted spider mites feed on many species of plants and are a major pest of vegetables, ornamentals, fruit trees, hops, cotton, and strawberries (van de Vrie et al., 1972). At present, it can be assumed that most of the major spider mite problems in greenhouses will involve twospotted spider mite. The larva, protonymph, deutonymph, and adult feed mainly on the undersides of the leaves.

It is within the scope of the present invention to provide a composition for controlling mite pests, particularly members of the Acari class, family Tetranychidae such as twospotted spider mite, more particularly spider mite species, especially the genera *Tetranychus, Panonychus* and various other mite species.

According to some embodiments of the present invention, the crop is selected from the group consisting of greenhouse grown crops and open field crops. Non limiting examples of crop types within the scope of the present invention include vegetables, fruit trees, hops, cotton and strawberries.

Specific examples of mite pests-host plant species within the scope of the present invention include the following:

Acanthaceae: *Acanthus mollis; Justicia adhatoda*.
Actinidiaceae: *Actinidia chinensis; Actinidia deliciosa; Actinidia* sp.
Adoxaceae: *Sambucus canadensis; Sambucus chinensis; Sambucus edulus; Sambucus nigra; Sambucus sieboldiana; Sambucus* sp.; *Viburnum lantana; Viburnum opulus; Viburnum rhytidophyllum; Viburnum* sp.; *Viburnum tinus*.
Aizoaceae: *Mesembryanthemum crystallinum*.
Alstroemeriaceae: *Alstroemeria* sp.
Amaranthaceae: *Alternanthera* sp.; *Amaranthus blitum; Amaranthus caudatus; Amaranthus graecizans; Amaranthus hybridus; Amaranthus mangostanus; Amaranthus palmeri; Amaranthus retroflexus; Amaranthus* sp.; *Amaranthus spinosus; Amaranthus viridis; Atriplex canescens; Atriplex lentiformis; Atriplex semibaccata; Beta vulgaris; Celosia argentea; Chenopodium album; Chenopodium murale; Chenopodium* sp.; *Dysphania ambrosioides; Haloxylon ammodendron; Iresine herbstii; Salsola vermiculata; Spinacia oleracea*.
Amaryllidaceae: *Allium ampeloprasum; Allium cepa; Allium fistulosum; Allium sativum; Allium* sp.; *Narcissus* sp.
Anacardiaceae: *Mangifera indica; Pistacia terebinthus; Pistacia vera*.
Annonaceae: *Annona muricata; Annona reticulata; Annona squamosa*.
Apiaceae: *Aegopodium podagraria; Ammi majus; Apium graveolens; Apium nodiflorum; Arracacia xanthorrhiza; Athamanta macedonica; Bupleurum lancifolium; Coriandrum sativum; Cryptotaenia canadensis;*

*Daucus carota; Eryngium* sp.; *Foeniculum vulgare; Pastinaca sativa; Petroselinum crispum; Peucedanum japonicum; Phellolophium madagascariense; Spananthe* sp.

Apocynaceae: *Ampelamus laevis; Apocynum cannabinum; Asclepias* sp.; *Catharanthus roseus; Mandevilla* sp.; *Matelea carolinensis; Nerium oleander; Plumeria* sp.; *Raphionacme* sp.; *Rauvolfia serpentina; Vinca major; Vinca* sp.

Aquifoliaceae: *Ilex crenata*.

Araceae: *Alocasia macrorrhizos; Alocasia* sp.; *Anthurium* sp.; *Arum italicum; Arum* sp.; *Caladium bicolor; Caladium* sp.; *Calla* sp.; *Colocasia esculenta; Colocasia* sp.; *Dieffenbachia* sp.; *Epipremnum pinnatum; Philodendron* sp.; *Symplocarpus foetidus; Xanthosoma* sp.; *Zantedeschia aethiopica*.

Araliaceae: *Aralia* sp.; *Hedera canariensis; Hedera helix; Hedera* sp.; *Hydrocotyle umbellata; Polyscias balfouriana; Schefflera actinophylla; Schefflera elegantissima; Schefflera* sp.; *Tetrapanax papyrifer*.

Araucariaceae: *Agathis* sp.; *Araucaria* sp.

Arecaceae: *Dypsis* sp.; *Phoenix dactylifera; Phoenix* sp.; *Veitchia* sp.

Aristolochiaceae: *Aristolochia clematitis*.

Asparagaceae: *Asparagus laricinus; Asparagus officinalis; Asparagus setaceus; Asparagus* sp.; *Aspidistra elatior; Cordyline fruticosa; Cordyline* sp.; *Dracaena braunii; Dracaena fragrans; Dracaena goldieana; Dracaena* sp.; *Hyacinthus orientalis; Lachenalia ensifolia; Maianthemum racemosum; Ornithogalum* sp.; *Polygonatum odoratum; Ruscus aculeatus; Yucca* sp.

Balsaminaceae: *Impatiens balsamina; Impatiens* sp.; *Impatiens walleriana*.

Berberidaceae: *Berberis cretica; Berberis thunbergii; Berberis vulgaris; Berberis wilsoniae; Nandina domestica*.

Betulaceae: *Alnus incana; Betula maximowicziana; Betula papyrifera; Betula pendula; Carpinus* sp.; *Corylus avellana*.

Bignoniaceae: *Campsis radicans; Pyrostegia venusta; Tecoma capensis; Tecoma stans*.

Boraginaceae: *Borago officinalis; Cynoglossum columnae; Heliotropium arborescens; Heliotropium eichwaldii; Heliotropium europaeum; Nama hispidum; Omphalodes verna*.

Brassicaceae: *Aethionema saxatile; Brassica juncea; Brassica napus; Brassica oleracea; Brassica rapa; Brassica* sp.; *Capsella bursa-pastoris; Diplotaxis erucoides; Diplotaxis viminea; Eruca vesicaria; Erysimum graecum; Erysimum* sp.; *Erysimum* x *cheiri; Hirschfeldia incana; Lepidium didymum; Malcolmia* sp.; *Matthiola fruticulosa; Matthiola incana; Matthiola odoratissima; Nasturtium* sp.; *Raphanus raphanistrum; Raphanus* sp.; *Rapistrum rugosum; Rorippa indica; Sinapis arvensis; Zilla spinosa*.

Bromeliaceae: *Tillandsia* sp.

Buxaceae: *Buxus sempervirens*.

Calophyllaceae: *Mammea americana*.

Campanulaceae: *Campanula erinus; Lobelia* sp.; *Platycodon grandiflorus*.

Cannabaceae: *Cannabis sativa; Celtis australis; Celtis occidentalis; Humulus lupulus; Humulus scandens; Trema micrantha*.

Cannaceae: *Canna indica*.

Capparaceae: *Capparis nummularia*.

Caprifoliaceae: *Cephalaria gigantea; Diervilla* sp.; *Leycesteria formosa; Lonicera etrusca; Lonicera nigra; Lonicera periclymenum; Lonicera* sp.; *Lonicera tatarica; Lonicera xylosteum; Pterocephalus plumosus; Scabiosa sicula; Symphoria racemosa; Symphoricarpos albus; Symphoricarpos orbiculatus; Weigela hortensis*.

Caricaceae: *Carica papaya*.

Caryophyllaceae: *Dianthus armeria; Dianthus barbatus; Dianthus caryophyllus; Dianthus chinensis; Dianthus* sp.; *Dianthus tenuiflorus; Drymaria cordata; Gypsophila paniculata; Myosoton aquaticum; Silene chalcedonica; Silene vulgaris; Stellaria media*.

Celastraceae: *Celastrus orbiculatus; Celastrus scandens; Euonymus europaeus; Euonymus japonicus; Euonymus* sp.

Cistaceae: *Helianthemum salicifolium*.

Cleomaceae: *Cleome* sp.; *Cleome viscosa*.

Clethraceae: *Clethra arborea*.

Combretaceae: *Terminalia catappa*.

Commelinaceae: *Commelina benghalensis; Commelina communis; Commelina diffusa*.

Compositae: *Acanthospermum hispidum; Achillea filipendulina; Achillea fraasii; Ageratum conyzoides; Ageratum houstonianum; Ambrosia trifida; Anthemis chia; Arctium lappa; Arctium minus; Arctotheca calendula; Arctotis* sp.; *Artemisia dracunculus; Bellis annua; Bidens bipinnata; Bidens biternata; Bidens pilosa; Bidens* sp.; *Boltonia* sp.; *Brachyscome* sp.; *Calendula arvensis; Calendula officinalis; Calendula* sp.; *Callistephus chinensis; Carduus crispus; Carthamus tinctorius; Centaurea cyanus; Centaurea hyalolepis; Centaurea iberica; Centaurea imperialis; Centaurea montana; Chaenactis stevioides; Chrysanthemum coronarium; Chrysanthemum indicum; Chrysanthemum morifolium; Chrysanthemum segetum; Chrysanthemum* sp.; *Chrysothamnus viscidiflorus; Cichorium endivia; Cichorium intybus; Cichorium pumilum; Cichorium spinosum; Conyza bonariensis; Conyza canadensis; Conyza* sp.; *Cosmos bipinnatus; Cosmos* sp.; *Crassocephalum crepidioides; Crepis neglecta; Crepis rubra; Cynara cardunculus; Cynara* sp.; *Dahlia coccinea; Dahlia* sp.; *Dahlia variabilis; Elephantopus mollis; Erigeron annuus; Erigeron* sp.; *Euryops* sp.; *Euthamia graminifolia; Galinsoga caracasana; Galinsoga ciliata; Galinsoga parviflora; Gerbera jamesonii; Gerbera* sp.; *Helianthella quinquenervis; Helianthus annuus; Helichrysum luteoalbum; Helichrysum tenax; Helichrysum thianschanicum; Heliopsis* sp.; *Helminthotheca echioides; Lactuca saligna; Lactuca sativa; Lactuca serriola; Lapsana communis; Leontodon autumnalis; Leucanthemum vulgare; Melampodium perfoliatum; Melanthera aspera; Mikania micrantha; Montanoa bipinnatifida; Notobasis syriaca; Osteospermum* sp.; *Parthenium* sp.; *Pentzia globosa; Picris pauciflora; Picris sprengeriana; Pseudognaphalium obtusifolium; Rudbeckia amplexicaulis; Rudbeckia* sp.; *Schkuhria pinnata; Scolymus maculatus; Scorzonera* sp.; *Senecio lividus; Senecio* sp.; *Senecio vulgaris; Solidago gigantea; Sonchus arvensis; Sonchus asper; Sonchus oleraceus; Sonchus* sp.; *Tagetes erecta; Tagetes microglossa; Tagetes minuta; Tagetes patula; Tagetes* sp.; *Taraxacum officinale; Tithonia rotundifolia; Tragopogon dubius; Tragopogon pratensis; Tridax procumbens; Urospermum dalechampii; Vernonia* sp.; *Xanthium strumarium; Zinnia elegans; Zinnia* sp.

Convolvulaceae: *Calystegia hederacea; Calystegia sepium; Convolvulaceae* sp.; *Convolvulus arvensis; Convolvulus hirsutus; Convolvulus scammonia; Con-*

*volvulus siculus; Convolvulus* sp.; *Convolvulus tricolor; Dinetus racemosus; Ipomoea aquatica; Ipomoea arachnosperma; Ipomoea batatas; Ipomoea biflora; Ipomoea cairica; Ipomoea hochstetteri; Ipomoea indica; Ipomoea lacunosa; Ipomoea lobata; Ipomoea nil; Ipomoea purpurea; Ipomoea* sp.; *Ipomoea tricolor; Ipomoea triloba.*

Cornaceae: *Cornus alba; Cornus canadensis; Cornus nuttallii; Cornus* sp.

Cucurbitaceae: *Benincasa hispida; Bryonia alba; Citrullus colocynthis; Citrullus lanatus; Cucumis melo; Cucumis sativus; Cucumis* sp.; *Cucurbita ficifolia; Cucurbita maxima; Cucurbita moschata; Cucurbita pepo; Cucurbita* sp.; Cucurbitaceae sp.; *Diplocyclos palmatus; Ecballium elaterium; Lagenaria siceraria; Luffa acutangula; Luffa cylindrica; Momordica charantia; Praecitrullus fistulosus; Sechium edule.*

Cupressaceae: *Chamaecyparis thyoides; Cupressus* sp.; *Juniperus arizonica; Juniperus virginiana; Platycladus orientalis.*

Cyperaceae: *Cyperus esculentus; Cyperus rotundus; Cyperus schimperianus.*

Dipterocarpaceae: *Shorea robusta.*

Ebenaceae: *Diospyros kaki; Diospyros scabrida.*

Elaeagnaceae: *Elaeagnus angustifolia; Elaeagnus umbellata.*

Equisetaceae: *Equisetum palustre.*

Ericaceae: *Azalea nudiflora; Azalea* sp.; *Rhododendron* sp.; *Siphonandra* sp.

Euphorbiaceae: *Acalypha australis; Acalypha havanensis; Acalypha* sp.; *Acalypha wilkesiana; Codiaeum* sp.; *Codiaeum variegatum; Croton niveus; Croton* sp.; *Euphorbia amygdaloides; Euphorbia burmanni; Euphorbia helenae; Euphorbia helioscopia; Euphorbia hirta; Euphorbia hypericifolia; Euphorbia parviflora; Euphorbia pulcherrima; Euphorbia* sp.; *Hevea brasiliensis; Hura crepitans; Jatropha gossypiifolia; Jatropha hastata; Jatropha multifida; Jatropha* sp.; *Manihot esculenta; Manihot* sp.; *Mercurialis annua; Mercurialis* sp.; *Ricinus communis.*

Fagaceae: *Quercus alba; Quercus robur; Quercus* sp.

Garryaceae: *Aucuba japonica.*

Gentianaceae: *Eustoma grandiflorum; Gentiana* sp.

Geraniaceae: *Erodium alnifolium; Geranium carolinianum; Geranium dissectum; Geranium lucidum; Geranium molle; Geranium rotundifolium; Geranium* sp.; *Pelargonium inquinans; Pelargonium* sp.

Gesneriaceae: *Saintpaulia ionantha.*

Goodeniaceae: *Goodenia* sp.; *Scaevola* sp.

Grossulariaceae: *Ribes americanum; Ribes nigrum; Ribes rubrum.*

Heliconiaceae: *Heliconia bihai; Heliconia latispatha.*

Hydrangeaceae: *Deutzia* sp.; *Hydrangea macrophylla; Hydrangea paniculata; Hydrangea* sp.; *Philadelphus coronarius; Philadelphus* sericanthus.

Iridaceae: *Crocosmia* x *crocosmiiflora; Gladiolus hortulanus; Gladiolus italicus; Gladiolus* sp.; *Iris sanguinea; Iris* x *germanica; Ixia flexuosa.*

Juglandaceae: *Carya illinoinensis; Juglans regia; Juglans* sp.

Lamiaceae: *Ajuga* sp.; *Ballota africana; Clerodendrum chinense; Clerodendrum thomsoniae; Galeopsis speciosa; Galeopsis tetrahit; Glechoma hederacea; Glechoma* sp.; *Holmskioldia sanguinea; Holmskioldia* sp.; *Lamium album; Lamium amplexicaule; Lamium purpureum; Lamium* sp.; *Lavandula* sp.; *Leonotis ocymifolia; Leucas martinicensis; Marrubium vulgare; Melissa officinalis; Mentha arvensis; Mentha* sp.; *Mentha spicata; Mentha* x *piperita; Moluccella laevis; Monarda fistulosa; Nepeta cataria; Ocimum basilicum; Ocimum tenuiflorum; Perilla frutescens; Rosmarinus officinalis; Salvia argentea; Salvia officinalis; Salvia pratensis; Salvia* sp.; *Salvia splendens; Salvia verticillata; Salvia viridis; Stachys arvensis; Vitex negundo.*

Lauraceae: *Cassytha* sp.; *Endlicheria paniculata; Laurus nobilis; Persea americana.*

Leguminosae: *Acacia greggii; Acacia horrida; Acacia huarango; Acacia karroo; Acacia robusta; Acacia* sp.; *Alysicarpus longifolius; Amphicarpaea bracteata; Anthyllis vulneraria; Arachis hypogaea; Arachis* sp.; *Astragalus sinicus; Bauhinia forficata; Bauhinia monandra; Bauhinia* sp.; *Bauhinia variegata; Bituminaria bituminosa; Canavalia ensiformis; Caragana arborescens; Cassia artemisioides; Ceratonia siliqua; Cercis siliquastrum; Cicer arietinum; Clianthus* sp.; *Clitoria ternatea; Coronilla valentina; Crotalaria juncea; Crotalaria micans; Crotalaria* sp.; *Dalbergia sissoo; Dalea mollis; Desmodium khasianum; Dolichos* sp.; *Erythrina corallodendron; Erythrina poeppigiana; Erythrina* sp.; *Genista* sp.; *Gleditsia* sp.; *Glycine max; Indigofera arrecta; Indigofera holubii; Indigofera tinctoria; Inga* sp.; *Kennedia coccinea; Lablab purpureus; Laburnum anagyroides; Laburnum* sp.; *Lathyrus cicera; Lathyrus odoratus; Lathyrus sativus; Lens culinaris; Lespedeza maximowiczii; Lotus corniculatus; Lupinus arboreus; Lupinus argenteus; Lupinus sativus; Macroptilium atropurpureum; Macroptilium lathyroides; Medicago arabica; Medicago arborea; Medicago lupulina; Medicago orbicularis; Medicago polymorpha; Medicago sativa; Medicago* sp.; *Melilotus albus; Melilotus indicus; Melilotus* sp.; *Mucuna membranacea; Mucuna pruriens; Neonotonia wightii; Neorautanenia mitis; Onobrychis viciifolia; Ornithopus* sp.; *Phaseolus acutifolius; Phaseolus coccineus; Phaseolus lunatus; Phaseolus* sp.; *Phaseolus vulgaris; Pisum sativum; Psophocarpus tetragonolobus; Pueraria montana; Pueraria phaseoloides; Rhynchosia capitata; Rhynchosia caribaea; Robinia hispida; Robinia pseudoacacia; Sesbania cannabina; Sesbania herbacea; Spartium junceum; Styphnolobium japonicum; Teramnus uncinatus; Tipuana tipu; Trifolium alexandrinum; Trifolium aureum; Trifolium dasyurum; Trifolium dubium; Trifolium glomeratum; Trifolium hybridum; Trifolium incarnatum; Trifolium pratense; Trifolium purpureum; Trifolium repens; Trifolium* sp.; *Trifolium spumosum; Vicia angustifolia; Vicia faba; Vicia pulchella; Vicia sativa; Vicia* sp.; *Vicia villosa; Vigna aconitifolia; Vigna angularis; Vigna mungo; Vigna radiata; Vigna* sp.; *Vigna unguiculata; Wisteria floribunda; Wisteria polystachya; Wisteria sinensis.*

Liliaceae: *Lilium* sp.

Linaceae: *Reinwardtia tetragyna.*

Lythraceae: *Cuphea* sp.; *Lagerstroemia speciosa; Punica granatum.*

Magnoliaceae: *Magnolia liliiflora; Magnolia* sp.; *Magnolia stellata.*

Malvaceae: *Abelmoschus esculentus; Abutilon pictum; Abutilon reflexum; Abutilon* sp.; *Abutilon theophrasti; Abutilon tubulosum; Alcea rosea; Althaea nudiflora; Byttneria australis; Ceiba pentandra; Corchorus capsularis; Corchorus olitorius; Gossypium barbadense; Gossypium herbaceum; Gossypium hirsutum; Gossypium* sp.; *Grewia asiatica; Grewia biloba; Helicteres*

*guazumifolia; Hibiscus lunariifolius; Hibiscus mutabilis; Hibiscus rosa-sinensis; Hibiscus* sp.; *Hibiscus syriacus; Hibiscus trionum; Hibiscus aegyptia; Malva moschata; Malva neglecta; Malva nicaeensis; Malva parviflora; Malva* sp.; *Malva sylvestris; Malva trimestris; Malvella leprosa; Sida rhombifolia; Sida* sp.; *Sterculia murex; Tilia americana; Tilia cordata; Tilia platyphyllos; Tilia rubra; Tilia* sp.; *Tilia tomentosa; Tilia* x *euchlora; Triumfetta semitriloba; Waltheria indica.*

Marantaceae: *Calathea* sp.; *Maranta* sp.

Meliaceae: *Azadirachta indica; Melia azedarach; Toona ciliata.*

Menispermaceae: *Tinospora fragosa.*

Moraceae: *Artocarpus altilis; Ficus carica; Ficus elastica; Ficus religiosa; Ficus* sp.; *Morus alba; Morus nigra; Morus rubra; Morus* sp.

Moringaceae: *Moringa oleifera.*

Musaceae: *Musa acuminata; Musa basjoo; Musa* sp.; *Musa* x *paradisiaca.*

Myrtaceae: *Eucalyptus grandis; Psidium cattleianum; Psidium guajava; Syzygium cumini.*

Nothofagaceae: *Nothofagus alpina.*

Nyctaginaceae: *Bougainvillea spectabilis.*

Olacaceae: *Ximenia americana.*

Oleaceae: *Forsythia koreana; Forsythia suspensa; Forsythia* x *intermedia; Fraxinus angustifolia; Fraxinus excelsior; Fraxinus ornus; Fraxinus* sp.; *Jasminum humile; Jasminum nudiflorum; Jasminum officinale; Jasminum sambac; Jasminum* sp.; *Ligustrum lucidum; Ligustrum vulgare; Olea europaea; Osmanthus fragrans; Syringa oblata; Syringa vulgaris.*

Onagraceae: *Chylismia claviformis; Epilobium angustifolium; Fuchsia magellanica; Fuchsia* sp.; *Fuchsia* x *hybrida; Gaura* sp.; *Oenothera biennis; Oenothera laciniata; Oenothera* sp.; *Oenothera tetraptera.*

Orchidaceae: *Catasetum* sp.; *Cymbidium* sp.; *Orchidaceae* sp.; *Papilionanthe teres.*

Oxalidaceae: *Oxalis corniculata; Oxalis debilis; Oxalis europaea; Oxalis floribunda; Oxalis* sp.

Papaveraceae: *Argemone mexicana; Bocconia frutescens; Chelidonium majus; Chelidonium* sp.; *Dicentra* sp.; *Eschscholzia* sp.; *Fumaria officinalis; Papaver aculeatum; Papaver nudicaule; Papaver orientale; Papaver rhoeas; Papaver somniferum.*

Passifloraceae: *Passiflora caerulea; Passiflora edulis; Passiflora foetida; Passiflora mollissima; Passiflora* sp.

Paulowniaceae: *Paulownia fortunei.*

Pedaliaceae: *Sesamum indicum.*

Phyllanthaceae: *Phyllanthus amarus; Phyllanthus* sp.

Phytolaccaceae: *Petiveria alliacea; Phytolacca americana; Phytolacca dioica; Phytolacca esculenta; Phytolacca icosandra.*

Pinaceae: *Pinus sylvestris; Tsuga canadensis.*

Pittosporaceae: *Pittosporum tobira.*

Plantaginaceae: *Angelonia* sp.; *Antirrhinum majus; Digitalis purpurea; Hippuris vulgaris; Linaria genistifolia; Mecardonia procumbens; Plantago asiatica; Plantago lanceolata; Plantago major; Plantago* sp.; *Veronica persica; Veronica* sp.; *Veronica teucrium.*

Platanaceae: *Platanus orientalis; Platanus* sp.

Plumbaginaceae: *Limoniastru guyonianum; Limonium sinuatum; Plumbago auriculata; Plumbago* sp.

Poaceae: *Aegilops* sp.; *Agropyron desertorum; Aira* sp.; *Avena fatua; Avena sativa; Avena* sp.; *Avena sterilis; Bambusa* sp.; *Bromus catharticus; Bromus* sp.; *Chondrosum barbatum; Cynodon dactylon; Dactyloctenium aegyptium; Digitaria argillacea; Digitaria ciliaris; Digitaria diversinervis; Digitaria sanguinalis; Eleusine coracana; Elymus hispidus; Elymus repens; Eragrostis* sp.; *Festuca arundinacea; Festuca* sp.; *Helictotrichon pratense; Hordeum* sp.; *Lolium multiflorum; Lolium* sp.; *Ophiuros exaltatus; Oryza glaberrima; Oryza sativa; Panicum miliaceum; Panicum* sp.; *Paspalum dilatatum; Pennisetum clandestinum; Pennisetum purpureum; Phleum pratense; Poa annua; Poa pratensis; Poa trivialis; Poaceae* sp.; *Rottboellia cochinchinensis; Saccharum officinarum; Setaria pumila; Setaria viridis; Sitanion hystrix; Sorghum bicolor; Sorghum halepense; Sorghum* sp.; *Stenotaphrum secundatum; Triticum* sp.; *Zea mays; Zeugites* sp.

Polemoniaceae: *Phlox carolina; Phlox paniculata; Phlox* sp.

Polygonaceae: *Emex australis; Fallopia baldschuanica; Fallopia convolvulus; Persicaria hydropiper; Persicaria longiseta; Persicaria maculosa; Persicaria pensylvanica; Polygonum argyrocoleon; Polygonum aviculare; Rumex acetosa; Rumex acetosella; Rumex crispus; Rumex japonicus; Rumex obtusifolius; Rumex* sp.

Pontederiaceae: *Eichhornia crassipes.*

Portulacaceae: *Portulaca oleracea.*

Primulaceae: *Cyclamen graecum; Cyclamen hederifolium; Cyclamen persicum; Cyclamen* sp.; *Primula denticulata; Primula polyantha; Primula* sp.; *Primula veris.*

Ranunculaceae: *Adonis aestivalis; Anemone coronaria; Anemone hortensis; Aquilegia* sp.; *Clematis paniculata; Clematis* sp.; *Delphinium* sp.; *Helleborus* sp.; *Ranunculus asiaticus; Thalictrum fendleri.*

Resedaceae: *Reseda odorata.*

Rhamnaceae: *Frangula dodonei; Helinus integrifolius; Rhamnus alpina; Rhamnus imeretina; Ziziphus jujuba; Ziziphus spina-christi.*

Rosaceae: *Alchemilla vulgaris; Armeniaca mume; Cerasus lusitanica; Cerasus serrula; Cerasus vulgaris; Chaenomeles japonica; Chaenomeles sinensis; Cotoneaster horizontalis; Cotoneaster microphyllus; Cotoneaster tomentosa; Crataegus laevigata; Crataegus monogyna; Crataegus sanguinea; Cydonia oblonga; Eriobotrya japonica; Filipendula ulmaria; Fragaria moschata; Fragaria vesca; Fragaria virginiana; Fragaria* x *ananassa; Geum rivale; Malus domestica; Malus floribunda; Malus pumila; Malus* sp.; *Marcetella maderensis; Padus avium; Potentilla fragarioides; Potentilla fruticosa; Potentilla norvegica; Potentilla tanacetifolia; Prunus amygdalus; Prunus armeniaca; Prunus avium; Prunus cerasifera; Prunus cerasoides; Prunus cerasus; Prunus domestica; Prunus insititia; Prunus lusitanica; Prunus persica; Prunus salicina; Prunus serotina; Prunus* sp.; *Prunus spinosa; Pyracantha coccinea; Pyracantha koidzumii; Pyracantha* sp.; *Pyrus communis; Pyrus pyrifolia; Pyrus* sp.; *Rosa canina; Rosa cymosa; Rosa hybrida; Rosa multiflora; Rosa odorata; Rosa rugosa; Rosa* sp.; *Rosa* x *alba; Rosa* x *centifolia; Rosa* x *damascena; Rosa* x *rugosa; Rubus buergeri; Rubus chaerophyllus; Rubus chingii; Rubus fruticosus; Rubus idaeus; Rubus lloydianus; Rubus occidentalis; Rubus* sp.; *Rubus ulmifolius; Sorbus aucuparia; Sorbus* sp.; *Spiraea japonica.*

Rubiaceae: *Coffea arabica; Coffea* sp.; *Galium aparine; Galium stellatum; Gardenia jasminoides; Gardenia* sp.

Rutaceae: *Choisya ternata; Citrus aurantiifolia; Citrus aurantium; Citrus clementina; Citrus limon; Citrus maxima; Citrus medica; Citrus paradisi; Citrus reticulata; Citrus sinensis; Citrus* sp.; *Citrus trifoliata; Ruta graveolens; Zanthoxylum rhoifolium.*

Salicaceae: *Dovyalis caffra; Populus alba; Populus nigra; Populus* sp.; *Populus tremula; Populus x canadensis; Salix aegyptiaca; Salix alba; Salix babylonica; Salix caprea; Salix chaenomeloides; Salix dephnoides; Salix fragilis; Salix* sp.; *Salix viminalis.*

Sapindaceae: *Acer campestre; Acer negundo; Acer platanoides; Acer pseudoplatanus; Acer rubrum; Acer saccharum; Acer* sp.; *Aesculus glabra; Dodonaea viscosa; Koelreuteria paniculata; Litchi sinensis; Sapindus* sp.

Saxifragaceae: *Rodgersia podophylla.*

Scrophulariaceae: *Buddleja davidii; Buddleja madagascariensis; Diascia* sp.; *Myoporum* sp.; *Nemesia* sp.; *Verbascum blattaria.*

Simaroubaceae: *Ailanthus altissima.*

Solanaceae: *Acnistus arborescens; Brugmansia arborea; Brugmansia suaveolens; Brugmansia x candida; Calibrachoa* sp.; *Capsicum annuum; Capsicum* sp.; *Cestrum cyaneum; Cestrum elegans; Cestrum strigillatum; Cyphomandra* sp.; *Datura metel; Datura* sp.; *Datura stramonium; Lycium chinense; Nicandra physalodes; Nicotiana glauca; Nicotiana* sp.; *Nicotiana tabacum; Petunia* sp.; *Petunia x hybrid; Physalis acutifolia; Physalis alkekengi; Physalis angulata; Physalis lagascae; Physalis peruviana; Salpichroa origanifolia; Solanum aethiopicum; Solanum americanum; Solanum capsicoides; Solanum carolinense; Solanum delagoense; Solanum elaeagnifolium; Solanum grandiflorum; Solanum laciniatum; Solanum lycopersicum; Solanum macrocarpon; Solanum mammosum; Solanum melongena; Solanum muricatum; Solanum nigrum; Solanum panduraeforme; Solanum quitoense; Solanum* sp.; *Solanum tuberosum; Withania somnifera.*

Strelitziaceae: *Strelitzia reginae.*

Theaceae: *Camellia japonica; Camellia sinensis; Camellia* sp.

Thymelaeaceae: *Dais cotinifolia.*

Tropaeolaceae: *Tropaeolum majus; Tropaeolum* sp.

Ulmaceae: *Ulmus americana; Ulmus glabra; Ulmus laevis; Ulmus pumila; Ulmus rubra; Ulmus* sp.

Urticaceae: *Boehmeria nivea; Laportea aestuans; Parietaria judaica; Parietaria officinalis; Pipturus albidus; Urtica dioica; Urtica* sp.; *Urtica urens.*

Verbenaceae: *Aloysia citriodora; Duranta erecta; Glandularia phlogiflora; Lantana camara; Lippia alba; Verbena bracteata; Verbena brasiliensis; Verbena hybrida; Verbena officinalis; Verbena* sp.

Violaceae: *Viola odorata; Viola* sp.; *Viola tricolor; Viola x wittrockiana.*

Vitaceae: *Ampelopsis* sp.; *Parthenocissus quinquefolia; Parthenocissus tricuspidata; Vitis* sp.; *Vitis vinifera.*

Xanthorrhoeaceae: *Hemerocallis fulva; Hemerocallis minor.*

Zingiberaceae: *Curcuma longa; Zingiber mioga.*

Zygophyllaceae: *Tribulus terrestris.*

The term "fungus reducing agent" or "fungal reducing agent" refers hereinafter to chemical fungus reducing agents such as a natural or synthetic fungicide, or to a biological fungus reducing agent such as a population of a mite species producing antifungal exudates, or a population of mycophagous mites.

It is within the scope of the current invention that the rearing composition as defined in any of the above is absent of or is lacking a fungus reducing agent. The claimed *Phytoseiulus* mites of the present invention are capable of completing their life cycle and reproducing for at least 2 generations when reared upon Astigmata non-living individuals including mites at any developmental stage and/or eggs. It is noted that the non-viable Astigmata mite developmental stages are incapable of producing or secreting a fungus reducing agent.

In order to understand the invention and to see how it may be implemented in practice, a plurality of preferred embodiments will now be described, by way of non-limiting example only, with reference to the following examples.

EXAMPLE 1

Protocol for Rearing *P. persimilis*

In this example, rearing is done by feeding *P. persimilis* with a mixture comprising dead frozen developmental stages of *C. lactis* and sawdust or another carrier material (e.g. bran). The prey mites were immobilized by an immobilization treatment, e.g. by freezing them or by a gamma irradiation treatment, prior to using them as food.

Exemplified Growth Conditions:

Temperature: in the range of 18° C.-30° C., particularly about 22° C.

Humidity: above 60%, particularly about 85%.

By using the aforementioned feeding regime, *P. persimilis* population was increased by an average of about 15%, per day.

Figure 3:
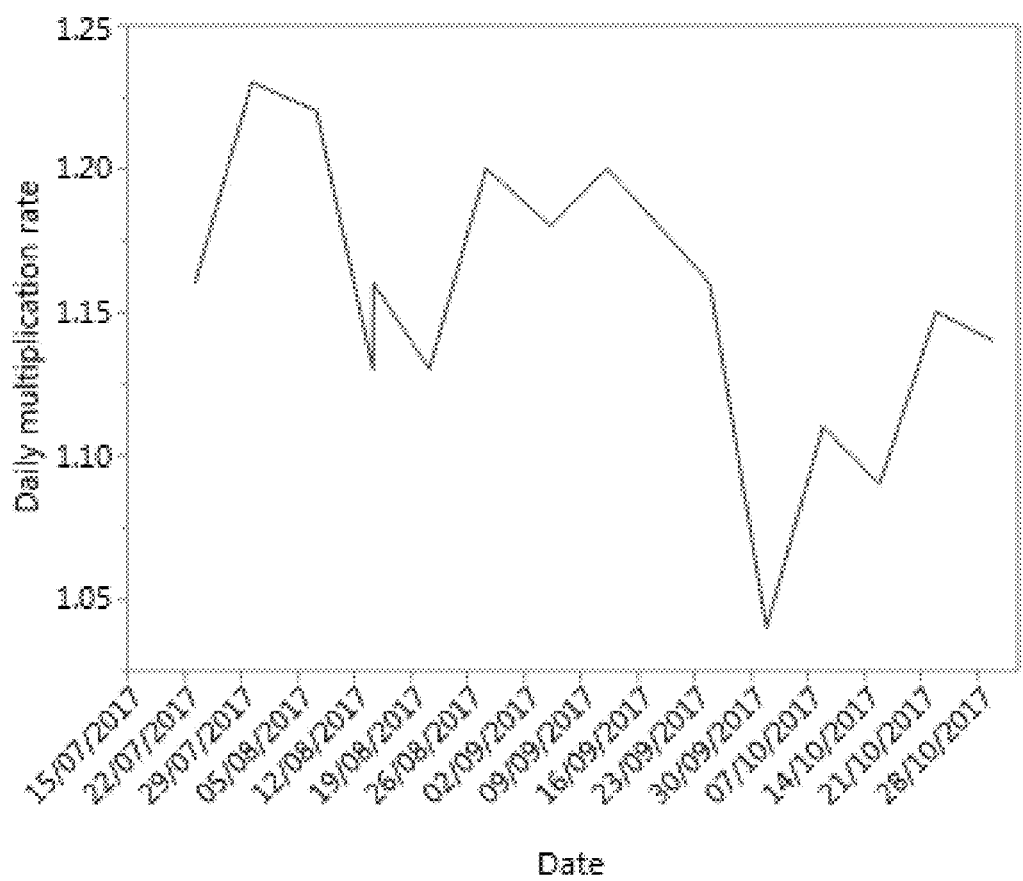
FIG. 3 is a graphic representation describing the daily multiplication rate of a *P. persimilis* population, feeding on a mixture of dead *C. lactis* eggs and dead mobile stages during a 14 weeks period.

FIG. 3 graphically describes the daily multiplication rate of *P. persimilis*, feeding on a mixture of dead *C. lactis* eggs and mobile stages (killed by freezing) during a 14 weeks period. As can be seen, an average increase of between about 10% and about 20% in multiplication rate of *P. persimilis* was recorded per day.

Methods Used for this Experiment:

A *P. persimilis* population was reared using dead *C. lactis* as prey at 22 degrees Celsius and 85% relative humidity in a mixture with sawdust. Every week the mixture was weighed, and four samples containing about 50 mg were taken, placed on a black adhesive tape and counted. Total population size was calculated according to these counts and 1500 individuals were left in the rearing each week. The multiplication rate was calculated by dividing the total number of the individuals found by 1500, giving the factor by which the population multiplied during this week. To switch to a daily multiplication rate, the 7th root of this number was taken according to the following formula:

$$\lambda = \sqrt[t]{\frac{N(t)}{N(0)}}$$

Where $\lambda$ is the daily multiplication rate, N(0) is the number of mites left in the rearing in the former count (1500 in this case), N(t) is the number of mites found at the current count, and t=7.

EXAMPLE 2

Rearing *P. persimilis* on Astigmatid Mite Species

In this experiment, different mite species were tested as food for *P. persimilis* using the following protocol:

30 P. persimilis mites were isolated in modified Munger cells, and served with frozen astigmatic mites of the species that are listed below. Food was replaced daily, and the mites were checked for feeding signs. The signs used as indicators were a full roundish body (contrary to a flat body of non-feeding mites), and whitish coloration in contrast to the usual orange color when feeding on spider mites.

Figure 4:
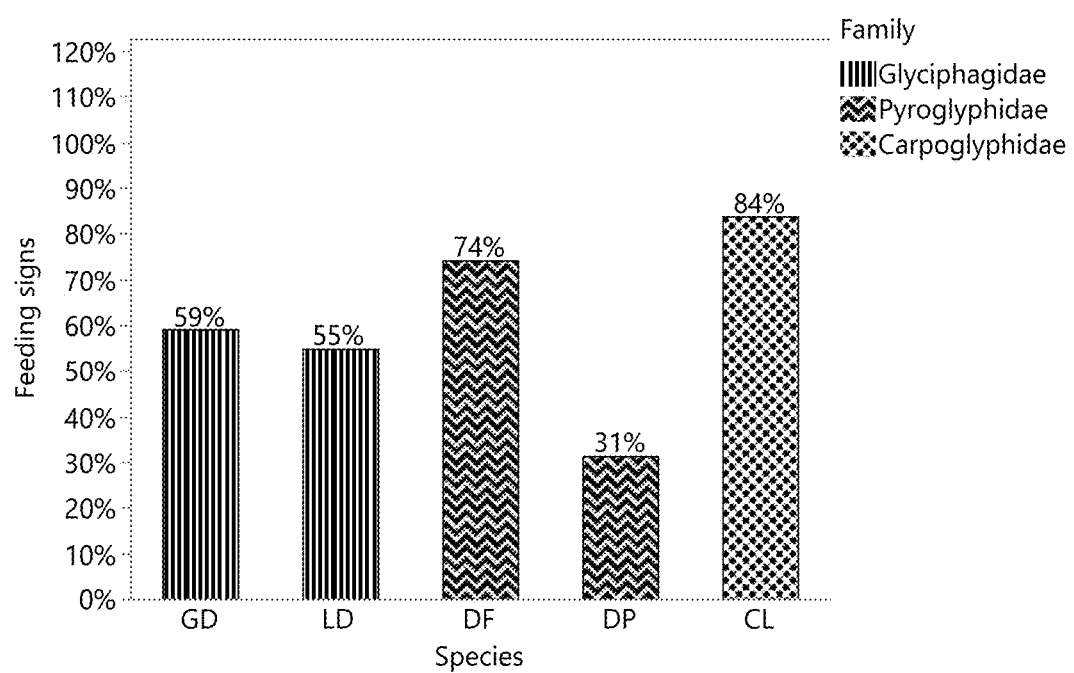
FIG. 4 is a graphic representation of the percentage of *P. persimilis* showing feeding signs, as appeared by their body's shape and color.

Reference is now made to FIG. 4 graphically presenting the percentage of P. persimilis showing feeding signs, as appeared by their body's shape and color, after given food for 3 consecutive days from each of the following prey species:

GD=*Glyciphagus domesticus* (Glycyphagidae family)
LD=*Lepidogyphus destructor* (Glycyphagidae family)
DF=*Dermatophagoides farinae* (Pyroglyphidae family)
DP=*Dermatophagoides pteronisinus* (Pyroglyphidae family)
CL=*Carpoglyphus lactis* (Carpoglyphidae family)

It can be seen that P. persimilis can feed on all of the above Astigmatic prey species, with varying efficiency.

EXAMPLE 3

Using *Amblyseius swirskii* as a Prey for P. persimilis

In this experiment, 50 predatory mites were given frozen mites of A. swirskii as food at 22 degrees Celsius, 85% RH, and checked daily. Mites were showing feeding signs by their large body shape and whitish coloration. When oviposition started, eggs were removed from the population, isolated, and hatchability was monitored. Hatching was noticed followed by maturation of the resulting larvae. When these mites matured, two were isolated to check for egg laying. These females did lay eggs, and hatching of the resulting eggs was observed. This demonstrates that P. persimilis can develop and reproduce on frozen A. swirskii as food for at least two generations, and that eggs laid at the third generation are viable.

EXAMPLE 4

Slow Release System for P. persimilis

Reference is now made to a description of a controlled release system for P. persimilis according to some embodiments of the present invention. Mixture containing about 200 P. persimilis mites reared on dead C. lactis prey and sawdust as a carrier was inserted into a container (e.g. sachet or a small plastic bottle of about 100 ml) with an exit hole in its lid. The container was placed on an adhesive tape or surface under controlled conditions (25 degrees Celsius and 75% humidity). The adhesive tape was replaced twice a week, and P. persimilis mites which appeared on it were counted to assess the release rate from the container.

Figure 8:
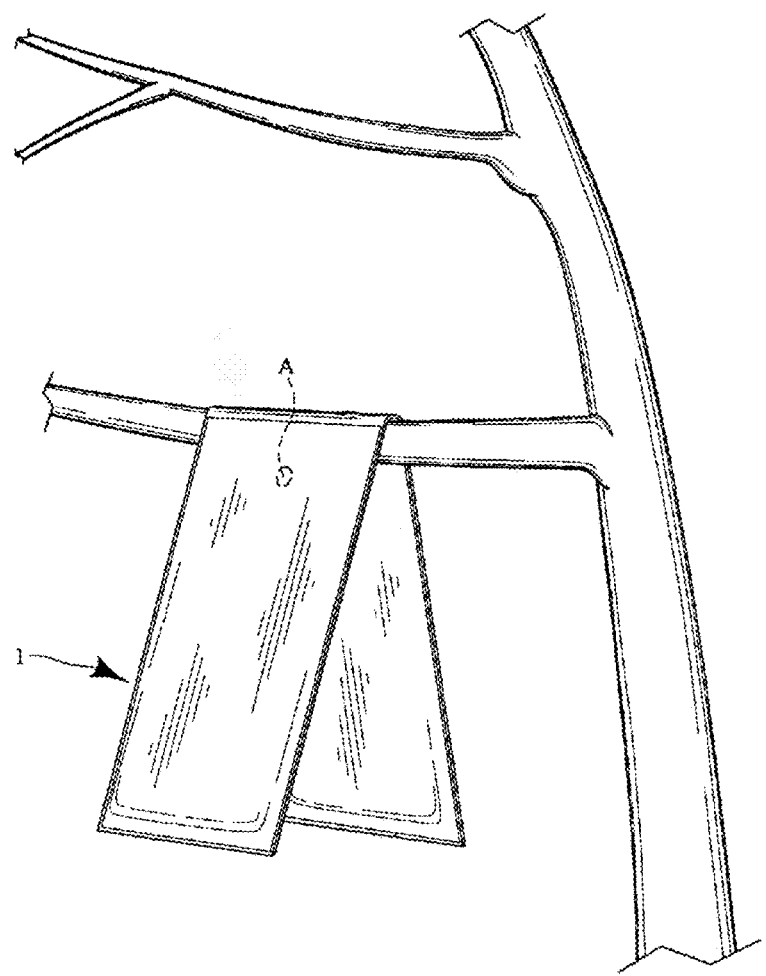
FIG. 8 schematically illustrates prior art sachet 1 with exit hole A for release of BCA in a cropping environment.

FIG. 8 shows an example of a prior art sachet, reproduced from U.S. Pat. No. 7,051,672, used for rearing and introducing a beneficial biological control agent, such as a predatory mite, to a cropping environment. The sachet is configured to be hung on the crop, allowing the rearing of the BCA within the sachet, and releasing the beneficial mites into the cropping environment.

Figure 5:
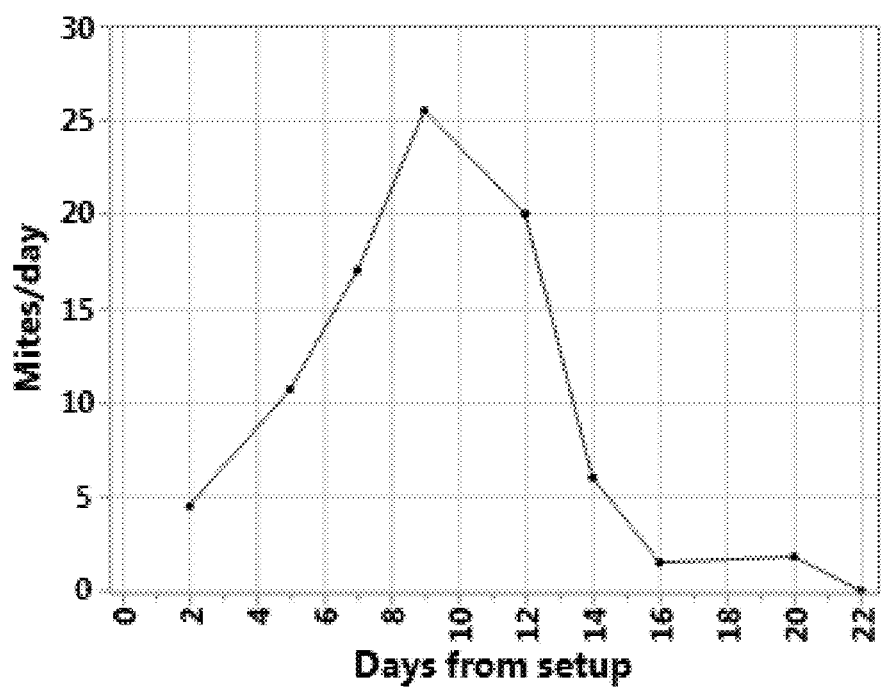
FIG. 5 graphically illustrates mites release rate as a function of number of days from experimental setup.

Reference is now made to FIG. 5 graphically illustrating mites release rate from the container as a function of the number of days since the setup of the experiment.

As can be seen in FIG. 5, mites are continuously released from the container for a period of 20 days, with a release peak occurring around day 9 (between days 8 and 10). The predatory mite release rate is between about 2 to 25 mites per day. This example demonstrates that a slow or controlled release system for P. persimilis (for at least about 20 days) is constructed, based on the rearing composition and method of the present invention.

EXAMPLE 5

*Phytoseiulus longipes* Reared on C. lactis as Prey

Reference is now made to an example in which rearing is done by feeding *Phytoseiulus longipes* (P. longipes), as a further representative example of the *Phytoseiulus* genus, with a mixture comprising dead C. lactis as a prey.

Exemplified rearing protocol: A P. longipes population was reared using dead C. lactis as prey at 22 degrees Celsius and 85% relative humidity in a mixture with sawdust. Mites showed feeding signs by changing their color from typical redish to white, as shown above for P. perdimilis fed on C. lactis (see FIGS. 1 and 2). In addition, all of the different life stages of the P. longipes mites have been observed, indicating that this species completed its development cycle on this alternative diet. The rearing was maintained for three weeks, showing that the P. longipes population can be reared upon dead C. lactis diet for at least this period of time.

EXAMPLE 6

Breeding and Selection for a P. persimilis Population with Increased Reproduction Rate on C. lactis as Prey This experiment shows successful breeding and selection for a P. persimilis population adapted for rearing on C. lactis as prey. As shown in this example, the selected P. persimilis population is characterized by advantageous and desirable properties of significantly increased reproduction rate when reared on Astigmatid mite individuals.

Experimental Protocol:

P. persimilis were reared using dead C. lactis as prey at 22 degrees Celsius and 85% relative humidity in a mixture with sawdust. Every week the mixture was weighed, and four samples containing about 50 mg each were taken, placed on a black adhesive tape and counted. Total population size was calculated according to these counts and 1500 individuals were left for rearing each week. The multiplication rate was calculated by dividing the total number of the individuals found, by 1500, giving the factor by which the population multiplied during this week. To calculate the daily multiplication rate, the $7^{th}$ root of this calculated number was taken according to the following formula:

$$\lambda = \sqrt[t]{\frac{N(t)}{N(0)}},$$

where $\lambda$ is the daily multiplication rate, N(0) is the initial number of mites left for rearing (i.e. 1500 mites), N (t) is the total number of mites found after rearing for a week period of time, and t=7.

It is noted that each population was maintained and measured for 4-10 weeks. The entire procedure was replicated for 3 times.

Figure 6:
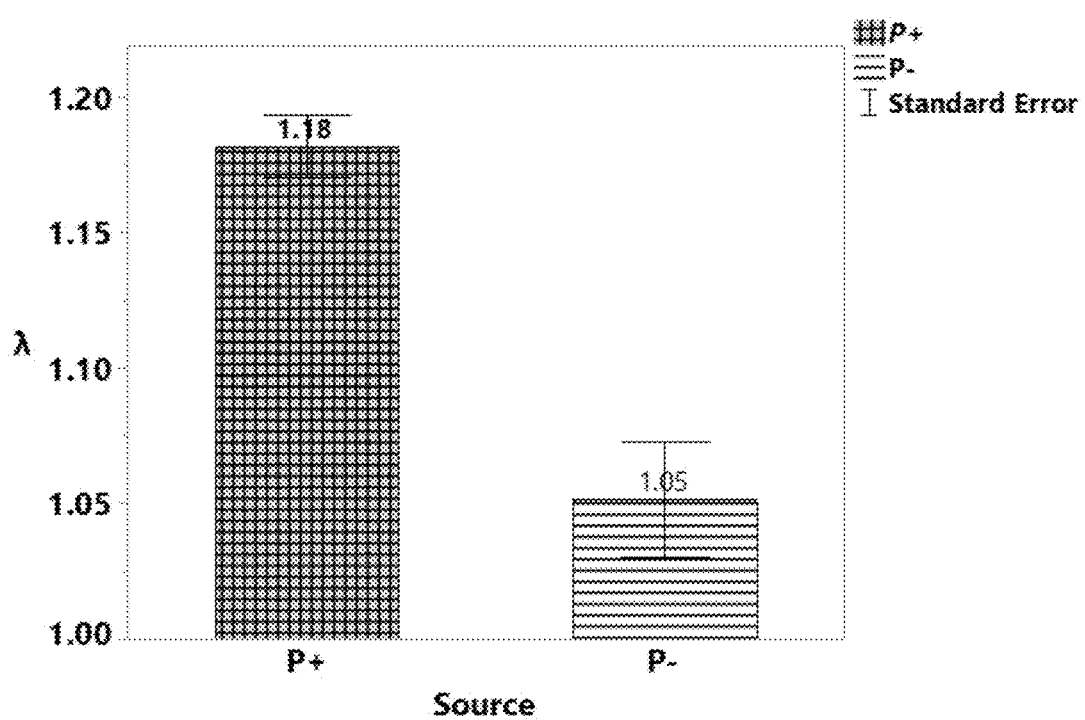
FIG. 6 graphically illustrates differences between daily reproduction rate of *P. persimilis* population sources (P+ and P−) reared upon *C. lactis* as a prey; the P+ population was bred and selected for improved adaptation for *C. lactis* as a prey; the P− population is the commercially available control *P. persimilis* population.

Reference is now made to FIG. 6 demonstrating the observed differences in the daily reproduction rate (represented by $\lambda$, the finite rate of increase) between the P. persimilis population bred and selected for adaptation for C. lactis as a factitious host prey (marked as P+ in FIG. 6), as compared to the conventional or commercially available P. persimilis population (reared upon its natural host, i.e. spider mites) used as a control (marked as P− in FIG. 6). The figure represents the means and the standard error found in the 2 values during the trial.

As can be seen in FIG. 6, the *P. persimilis* population subjected to selection for improved adaptation to rearing upon *C. lactis* individuals (P+) demonstrated a significant increased daily reproduction rate of about 3.6 fold (P+/P−: 0.18/0.05) on *C. lactis* as a prey, as compared to the control *P. persimilis* population, not subjected to the breeding and selection process as inter alia described (P−).

To conclude, the present invention provides for the first time a *P. persimilis* population characterized by increased reproduction rate trait when reared upon Astigmatid mites such as *C. lactis* individuals as a prey. This enables the highly desirable, revolutionary, indoor production of improved *P. persimilis* predatory mites exhibiting increased yield when reared upon Astigmata species, as compared to non-selected currently available *P. persimilis* mites, which demonstrate significantly reduced reproduction rate and yield when reared upon the same Astigmata species prey.

EXAMPLE 7

Slow Release of the Mites in the Field

This example shows the performance of a slow release system of the current invention (e.g. as described in Example 4 above) in greenhouse conditions.

Sweet pepper plants were planted in the greenhouse, and exposed to three different treatments in 5 replicates:

a) A slow release sachet containing 30 *P. persimilis* individuals was applied to the plants 13 days before the plants were infested with spider mites.

b) A slow release sachet containing 30 *P. persimilis* individuals was applied to the plants 6 days before the plants were infested with spider mites.

c) Control plants which were not exposed to *P. persimilis*.

The sachet was located on the lower parts of 1 meter tall plants. Infestation was carried out by stapling an infested leaf with spider mites to one of the top leaves of the plant. The mite population on each plant was sampled 3 days after the plants were infested. The spider mites and *P. persimilis* mites found on the infested leaf or above it were counted.

Figure 7:
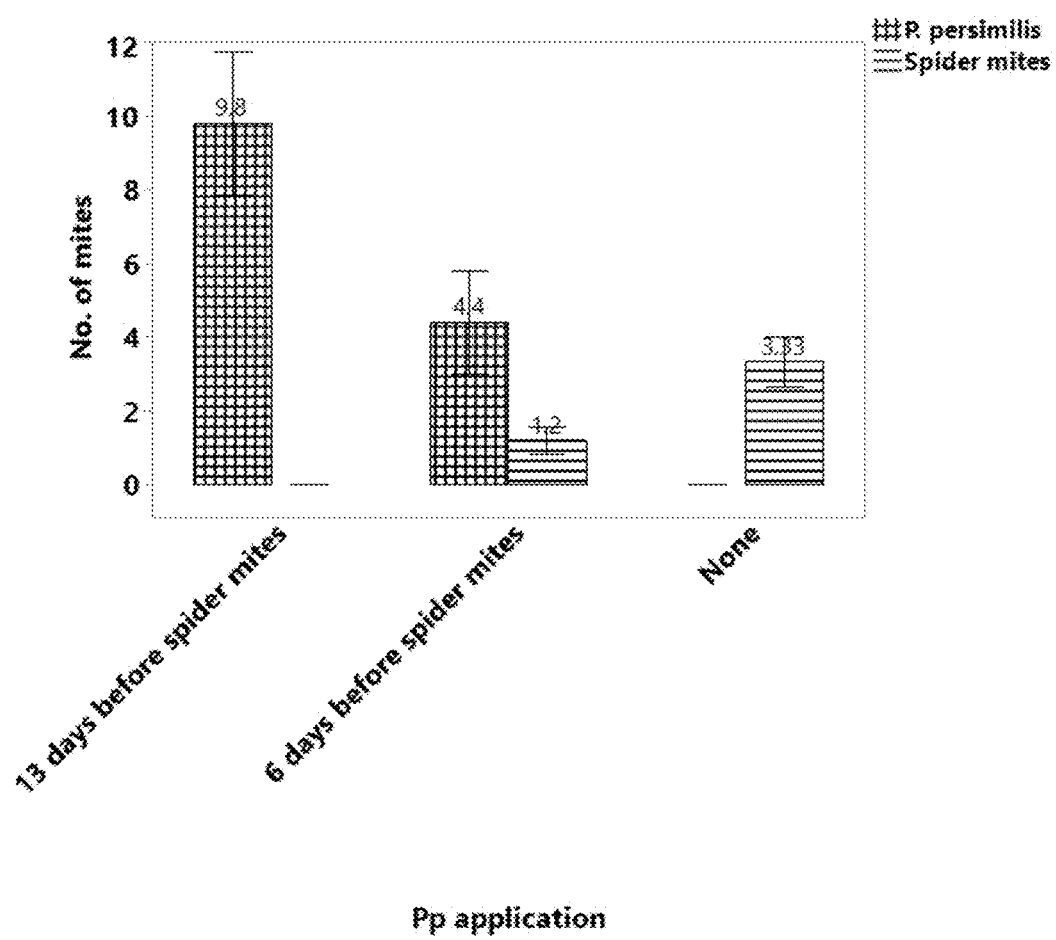
FIG. 7 graphically illustrates *P. persimilis* (Pp) and spider mite counts of plants exposed to the slow release system of the present invention, as compared to control plants.

Reference is now made to FIG. 7 graphically illustrating *P. persimilis* (Pp) and spider mite counts of plants exposed to the slow release system of the present invention as compared to control plants. As can be seen, the predatory mites were found on plants exposed to both of the *P. persimilis* treatments. Furthermore, the amounts of spider mites in the *P. persimilis* treated plants were rapidly reduced compared to the control plants. More particularly, an inverse correlation was observed between the *P. persimilis* counts and the spider mites counts, namely, the more *P. persimilis* mites were found on the plants, the less spider mites were counted. This experiment clearly demonstrates that *P. persimilis* mites, and more specifically, the composition of the present invention, are effective against spider mite infestation. The *P. persimilis* slow release system of the present invention reduced the spider mites population on the plant, despite the relatively long time (about 6 to 13 days) elapsing between the *P. persimilis* application and the spider mites arrival to the plant. This shows the effectiveness of the *P. persimilis* composition and slow release system as herein described in controlling spider mite infestations.

REFERENCES

Chant, D. A. & McMurtry, J. A. (2006). A review of the subfamily Amblyseiinae Muma (Acari: Phytoseiidae): part VIII. The tribes Macroseiini Chant, Denmark and Baker, Phytoseiulini n. tribe, Africoseiulini n. tribe and Indoseiulini Ehara and Amano. International Journal of Acarology 32, 13-25.

Simmonds, S. P. (1970). The Possible Control of *Steneotarsonemus pallidus* on Strawberries by *Phytoseiulus persimilis*. Plant pathology 19, 106-107.

McMurtry, J. A. & Croft, B. A. (1997). Life-styles of phytoseiid mites and their roles in biological control. Annual Review of Entomology, 42, 291-321.

Helle, W. & Sabelis, M. W. (1985). Spider Mites. Their Biology, Natural Enemies and Control, Vol. 1B. Elsevier, Amsterdam.

Gerson, U., Smiley, R. L. & Ochoa, R. (2003). Mites (Acari) for Pest Control; Blackwell Science Ltd.: Oxford, UK.

Walzer, A. & Schausberger, P. (1999). Cannibalism and interspecific predation in the phytoseiid mites *Phytoseiulus persimilis* and *Neoseiulus californicus*: predation rates and effects on reproduction and juvenile development BioControl 43:457-468.

Yao, D. S. & Chant, D. A. (1989). Population growth and predation interference between two species of predatory phytoseiid mites (Acarina: Phytoseiidae) in interactive systems. Oecologia 80:443-455.

Walzer, A., Paulus, W. & Schausberger, P. (2004) Ontogenetic shifts in intraguild predation on thrips by phytoseiid mites: the relevance of body size and diet specialization. Bulletin of Entomological Research, 94, 577-584.

van de Vrie, M., McMurtry J. A. & Huffaker C. B. (1972) Ecology of tetranychid mites and their natural enemies: A review: III. Biology, ecology, and pest status, and host-plant relations of tetranychids. Hilgardia 41(13): 343-432.

The invention claimed is:

1. A rearing composition comprising:
a predatory mite population of at least one mite species of the genus *Phytoseiulus*, and a prey mite population of individuals of at least one mite species from the order Astigmata, wherein said predatory mite population will oviposit for at least 2 generations on said Astigmata prey, further wherein said Astigmata prey is selected from the group consisting of non-viable eggs and a combination of non-viable eggs and non-viable mites of any developmental stage.

2. The rearing composition of claim 1, wherein said predatory mite population exhibits a daily reproduction rate in the range of 1.15-1.20.

3. The rearing composition of claim 1, wherein said composition is absent of a fungus reducing agent.

4. The rearing composition of claim 1, wherein said predatory mite species is selected from the group consisting of *Phytoseiulus fragariae, Phytoseiulus longipes, Phytoseiulus macropilis, Phytoseiulus persimilis* and *Phytoseiulus robertsi*.

5. The rearing composition of claim 1, wherein the species from the order Astigmata comprises members from a family selected from Carpoglyphidae, Glycyphagidae, Pyroglyphidae, and Acaridae.

6. The rearing composition of claim 1, wherein said Astigmata prey population is in a frozen form.

7. The rearing composition of claim 1, wherein said Astigmata prey population comprises a mixture comprising non-viable developmental stages of juvenile mites.

8. The rearing composition of claim 1, wherein said composition further comprises sawdust, bran or another carrier material.

9. The rearing composition of claim 1, wherein said predator population reared on said mite species from the order Astigmata, is reproduced at a rate of 15% to 25% per day.

10. The rearing composition of claim 1, wherein said Astigmatid individuals are treated by a treatment selected from the group consisting of: thermal treatment, chemical treatment, radiation treatment, mechanical treatment, gas pressure treatment, electrical treatment, immobilizing with an adhesive, immobilization by starvation, immobilization by suffocation or anoxia treatment, and any combination thereof.

11. The rearing composition according to claim 1 formulated for controlled release of said predatory mites on a crop plant.

12. A method for rearing predatory mite population comprising at least one mite species of the genus *Phytoseiulus*, the method comprising:
   a. providing a composition according to claim 1; and
   b. allowing individuals of the predatory mite population to prey on individuals of the Astigmatid population for at least 2 generations.

13. The method according to claim 12, wherein the rearing population is maintained at a temperature range of 18-30° C.

14. The method according to claim 12, wherein the rearing population is maintained at a relative humidity of 70-90%.

15. A method for controlling a crop pest, the method comprising applying a composition according to claim 1 to a field crop.

16. The method according to claim 15, wherein said crop pest is selected from the group of mite pests of the Acari family Tetranychidae.

17. The method according to claim 16, wherein the crop pest is from the genus *Tetranychus* or *Panonychus*.

18. A biological control agent (BCA) for controlling crop pests comprising at least one predatory mite species of the genus *Phytoseiulus* raised by the composition according to claim 1.

19. A container containing the composition according to claim 1, said container configured to be hung on a crop plant, said container comprises an exit hole from which said predatory mites are slowly and continuously released to said crop during a period of about three weeks.

* * * * *